United States Patent [19]

Pepin et al.

[11] Patent Number: 5,475,132

[45] Date of Patent: * Dec. 12, 1995

[54] ANTIFUNGAL AGENTS BASED ON AMIDES CONTAINING A PHENYL GROUP

[75] Inventors: Regis Pepin, Rilleux la Pape; Christian Schmitz, Anse; Guy-Bernard Lacroix, Lyon; Philippe Dellis, St. Didier au Mont d'Or; Christine Veyrat, St. Cyr au Mont d'Or, all of France

[73] Assignee: Rhone-Poulenc Agrochimie, Lyon, France

[*] Notice: The portion of the term of this patent subsequent to Aug. 30, 2011, has been disclaimed.

[21] Appl. No.: 250,599

[22] Filed: May 27, 1994

Related U.S. Application Data

[63] Continuation of Ser. No. 816,678, Jan. 3, 1992, Pat. No. 5,342,835, which is a continuation of Ser. No. 401,939, Sep. 1, 1989, abandoned.

[30] Foreign Application Priority Data

| Sep. 1, 1988 | [FR] | France | 88 11665 |
| Apr. 25, 1989 | [FR] | France | 89 05774 |
| Jul. 3, 1989 | [FR] | France | 89 09150 |
| Jul. 13, 1989 | [FR] | France | 89 09742 |

[51] Int. Cl.⁶ .................. C07C 65/105; C07C 69/94
[52] U.S. Cl. .................. 560/59; 549/79; 549/365; 549/447; 560/11; 560/18; 560/45; 560/47; 560/48; 560/51; 560/76; 560/102; 562/429; 562/432; 562/452; 562/456; 562/457; 562/459; 562/469; 562/488; 562/492
[58] Field of Search .............. 560/59, 102; 56/469, 56/492; 549/365, 447

[56] References Cited

U.S. PATENT DOCUMENTS

| 3,049,564 | 8/1962 | Waring | 564/161 |
| 3,592,907 | 7/1971 | Chandler, Jr. et al. | 424/275 |
| 3,697,508 | 10/1972 | Yamamoto et al. | 260/239.3 |
| 3,927,037 | 12/1975 | Scherrer | 260/346.2 R |
| 3,944,672 | 3/1976 | Steinman | 424/74 |
| 4,473,709 | 9/1984 | Montgomery et al. | 564/282 |
| 5,342,835 | 8/1994 | Pepin et al. | 514/227.5 |

FOREIGN PATENT DOCUMENTS

| 0003663 | 8/1979 | European Pat. Off. |
| 0135770 | 4/1985 | European Pat. Off. |
| 0146243 | 6/1985 | European Pat. Off. |
| 0169712 | 1/1986 | European Pat. Off. |
| 0177287 | 4/1986 | European Pat. Off. |
| 0182302 | 5/1986 | European Pat. Off. |
| 0230946 | 8/1987 | European Pat. Off. |
| 0251315 | 1/1988 | European Pat. Off. |
| 2151576 | 4/1973 | France |
| 3643403 | 6/1988 | Germany |
| 3710717 | 10/1988 | Germany |

OTHER PUBLICATIONS

Chemical Abstracts, vol. 75, No. 1, Jul. 5, 1971, p. 474, Abstract No. 5700m.
Chemical Abstracts, vol. 89, No. 19, Nov. 6, 1978, p. 560, Abstract No. 163396k.
Chemical Abstracts, vol. 90, No. 9, Feb. 26, 1979, p. 503, Abstract No. 72053a.
Bulletin de La Societe Chimique de France, Mar.–Apr. 1974 (3–4), second part, pp. 475–476.
Chimie Therapeutique, vol. 8, No. 4, Jul.–Aug. 1973, pp. 398–411.
Tetrahedron Letters, No. 41, Oct. 1971, pp. 3825–3828.
Chemical Abstracts, vol. 91, No. 7, Aug. 13, 1979, p. 666, Abstract No. 56566k.
Chemical Abstracts, vol. 79, No. 25, Dec. 24, 1973, pp. 291–292, Abstract No. 146100k.
Canadian Journal of Chemistry, vol. 65, No. 1, Jan. 1987, pp. 18–20.
Chemical Abstracts, vol. 111, No. 11, Sep. 11, 1989, p. 730, Abstract No. 97105j.

Primary Examiner—Richard L. Raymond
Attorney, Agent, or Firm—Burns, Doane, Swecker & Mathis

[57] ABSTRACT

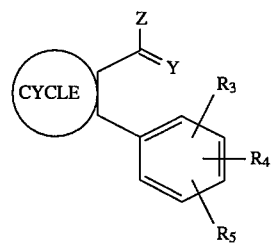

FORMULA I in which:

CYCLE surrounded by a semicircle represents, with the two carbon atoms to which the semicircle is linked, a carbon-containing, optionally heterocyclic, ring containing at least one ethylenic or aromatic bond between the two carbon atoms which carry the —C(Z)=Y group and the phenyl group, Y is oxygen or sulphur, Z is $NR_1R_2$, $R_1$ and $R_2$, each represents optionally substituted alkyl, alkoxy or cycloalkyl; alkenyl or alkynyl; or —$NR_1R_2$ represents saturated or unsaturated heterocyclyl;

$R_3$, $R_4$ and $R_5$, each represents a hydrogen or halogen atom (at least one of $R_3$, $R_4$ and $R_5$ being other than hydrogen or halogen); optionally substituted amino; optionally halogenated or hydroxylated alkyl, alkoxy, alkylalkoxy or alkylthio; or $R_3$ and $R_4$ (in the 3- and 4-positions) can together form a single divalent radical with 3 or 4 members containing 1 or 2 non-adjacent oxygen atoms; are useful as agricultural fungicides.

6 Claims, No Drawings

ANTIFUNGAL AGENTS BASED ON AMIDES CONTAINING A PHENYL GROUP

This application is a continuation of application Ser. No. 07/816,678, filed Jan. 3, 1992, now U.S. Pat. No. 5,342,835, which is a continuation of application Ser. No. 07/401,939, filed Sep. 1, 1989, now abandoned.

The present invention relates to new derivatives with phenyl and amide groups (and their homologues), to processes for their preparation, to their use in the protection of plants against fungal attacks, to intermediate products useful in their manufacture and to their preparation.

In the present description, the various formulae mentioned are presented together at the end of the text (before the claims). The term lower applied to radicals containing a carbon chain signifies that that carbon chain has from one to four carbon atoms (or from 2 to 4 carbon atoms in unsaturated carbon chains).

The present invention accordingly provides amide derivatives of formula (I) in which:

CYCLE surrounded by a semicircle represents, with the two carbon atoms to which the semicircle is linked, a 4 to 7 (preferably 5 or 6) membered carbon-containing, optionally heterocyclic, ring comprising an ethylenic or aromatic unsaturated bond between the two carbon atoms which carry the

group
and the phenyl group, which ring is optionally substituted, for example, by organic radicals having at most 30 carbon atoms;

Y is an oxygen or sulphur atom;

Z is a chlorine atom or an OW', $NHR_1$ or $NR_1R_2$ group (the compounds in which Z is $NR_1R_2$ are preferred when it is desired to combat plant diseases, and the compounds in which Z is a chlorine atom, an OW' group or an $NHR_1$ group are principally useful as chemical intermediates);

W' is a hydrogen atom, a lower alkyl radical or an alkali or alkaline-earth metal atom;

$R_1$ and $R_2$, which are identical or different, each represents:

a lower alkyl or lower alkoxy radical (at least one of $R_1$ and $R_2$ being other than alkoxy) or a cycloalkyl radical having from 3 to 7 carbon atoms, which radicals are optionally substituted by halogen, hydroxyl, lower alkoxy, (lower) alkoxy-(lower) alkyl, (lower) acyloxy or phenyl, or a 4 to 6 membered heterocyclic group containing 1 or 2 oxygen, nitrogen or sulphur atoms or an amino group which is mono- or disubstituted by lower alkyl, an alkenyl or alkynyl radical having from 3 to 7 carbon atoms, or $R_1$ and $R_2$, together with the nitrogen atom to which they are attached, form a 4 to 7 (preferably 5 or 6) membered heterocycle, which is saturated or unsaturated, and contains 1, 2 or 3 oxygen, sulphur or nitrogen atoms, and is optionally substituted by lower alkyl, lower alkoxy, hydroxyl, oxo, one or more halogen atoms, or (lower) alkyl-(lower) alkoxy;

$R_3$, $R_4$ and $R_5$, which are identical or different, each represents:

a hydrogen or halogen atom, at least one of these radicals $R_3$, $R_4$ and $R_5$ being other than a hydrogen or halogen atom an amino group which is optionally substituted by one or two lower alkyl groups a lower alkyl, lower alkoxy, (lower) alkyl(lower) alkoxy or lower alkylthio group, each of which is optionally halogenated or hydroxylated; or $R_3$ and $R_4$ (in the 3- and 4- positions) can together form a single divalent radical with 3 or 4 members containing 1 or 2 non-adjacent oxygen atoms.

The present invention relates more specifically, as compounds which are useful, in particular, for combating fungal attacks on plants, to the compounds of formula (I) in which Z is $NR_1R_2$, and in which the various radicals and substituents are chosen, in their nature and in their position, such that the decimal logarithm (log P) of their octanol/water partition coefficient (P) is from 2 to 5, preferably from 2.5 to 4.5.

The octanol/water partition coefficient P of a chemical compound is determined according to methods which are known per se.

The coefficient is the ratio of the equilibrium concentrations of a substance dissolved in a two-phase system constituted of the two immiscible solvents, octanol and water, that is to say that:

$$P = \frac{C \text{ octanol}}{C \text{ water}}$$

Measurement is carried out at 20° C., and at three different concentrations and three different phase ratios, it being understood that the same value of P should be found at these three concentrations and these three phase ratios.

If it is a question of a compound which is more soluble in water, three aqueous solutions of the compound are prepared at concentrations of 0.25 g/l, 0.5 g/l and 1 g/l, and each of these solutions is mixed with octanol in such a quantity that the aqueous solution of compound/octanol volume ratio is respectively 80:20, 90:10 and 95:5. These mixtures are then stirred and decanted, and in each of them the quantity of dissolved compound is measured by high performance liquid chromatography and the partition coefficient is determined according to the formula indicated above.

Conversely, if it is a question of a compound which is more soluble in octanol, three octanolic solutions of the compound are prepared at respective concentrations of 0.25 g/l, 0.5 g/l and 1 g/l, end each of these solutions is mixed with water in such a quantity that the octanolic solution of compound/water volume ratio is respectively 80:20, 90:10, 95:5.

If the compound is too sparingly soluble both in water and in octanol, so that in neither of them can concentration levels equal to 0.25, 0.5 and 1 g/l be attained, then the determination is carried out at lower concentration ranges, for example 0.05, 0.1 and 0.2 g/l, or still lower.

However it is achieved, three values of P, which should be identical, are thus obtained under these conditions (if they are not identical, lower concentrations are found which allow three equal values to be arrived at) and this unique value which is common to the three measurements corresponds to the partition coefficient P (or to its logarithm log P) which characterizes the compound.

However, in practice, it has become common to replace this measurement of partition coefficient by its value calculated from the structure of the molecule. Indications on the calculation methods are provided by C. Hansch and A. Leo in the book "Substituent Constants for Correlation Analysis in Chemistry and Biology" Ed. John Wiley 1979, pages 18 to 43. This method has evolved slightly during the years, but in the sense of a refinement, that is to say of a greater proximity to the real value obtained by direct measurement.

Thus, the method of calculating the partition coefficient has been improved to take account of the correction factors for interactions (A. Leo, J. Chem. Perkin Trans. II pages 825–838, 1983). To facilitate these calculations computer programs are sold which themselves directly carry out the calculation of the partition coefficient (log P). Thus, in the present text, values provided by the "Medchem" program, which is described in the "Medchem Software Manual, release 3.52" of November 1987, which is edited by Pomona College at Claremont in California, have been used.

Even if such a computer program should evolve in future, its evolution will go in the direction of greater exactitude, that is to say of increasing closeness to the experimental value of log P.

The principle of replacement of the measured value by the calculated value of log P is so common that this method is accepted by the Environmental Protection Agency in the USA.

In the present text, values of log P calculated an indicated above have therefore been used.

In this specification and the accompanying claims, when a meaning of multiple radicals is indicated, for example by $(R)_n$, that is to say n times the radical R, it is to be understood that the various radicals R can be identical or different; this is so for all the types of radicals and substituents.

Among the large family of compounds of formula (I) various sub-families are particularly advantageous.

Thus, compounds are preferred which have one or more of the following characteristics:

$R_1$ and $R_2$, which are identical or different, each represents:

a lower alkyl radical, a cycloalkyl radical having from 3 to 7 carbon atoms; an alkenyl or alkynyl radical having from 3 to 7 carbon atoms; an alkoxyalkyl radical having from 3 to 8 carbon atoms or $R_1$ and $R_2$, together with the nitrogen atom to which they are attached, form a 4 to 7 membered saturated or unsaturated heterocycle which contains one or two oxygen, nitrogen or sulphur atoms and is optionally substituted by alkyl radicals having from 1 to 3 carbon atoms or alkoxyalkyl groups having from 2 to 4 carbon atoms.

$R_3$, $R_4$ and $R_5$ are, respectively, in the 3-, 4- and 5-positions on the phenyl group substituting the CYCLE (these positions being numbered with respect to the valency bond linking the phenyl group with the CYCLE), and $R_3$, $R_4$ and $R_5$, which are identical or different, each represents a hydrogen or halogen atom (at least one of these 3 radicals being other than the hydrogen or halogen atom); or a lower alkyl or lower alkoxy radical; alkoxyalkyl having from 2 to 4 carbon atoms; lower alkylthio; hydroxyl; or an amino group which is optionally monosubstituted or disubstituted by lower alkyl, or $R_3$ and $R_4$ (in the 3- and 4- positions) can together form a single divalent radical with 3 or 4 members containing 1 or 2 non-adjacent oxygen atoms, CYCLE, surrounded by a semicircle, represents a divalent radical —$K_6$—$K_7$—$K_8$—$K_9$— or —$K_6$—$K_7$—$K_{10}$— so as to constitute, with the two carbon atoms to which it is attached, a 5- or 6-membered ring [as shown in formulae (Ia) and (Ib)], the $K_6$, $K_7$, $K_8$, $K_9$ and $K_{10}$ groups being such that:

$K_6$ represents —N= or —C($R_6$)=
$K_7$ represents —N= or —C($R_7$)=
$K_8$ represents —N= or —C($R_8$)=
$K_9$ represents —N= or —C($R_9$)=
$K_{10}$ represents —N= or —C($R_{10}$)=
and, in addition, when CYCLE surrounded by a semicircle represents —$K_6$—$K_7$—$K_{10}$—, the radicals $K_6$, $K_7$ and $K_{10}$ can also be such that:

$K_6$ represents —N($R_6$)—, —C($R_6$)$_2$—, —O— or —S(O)$_n$
$K_7$ represents —N($R_7$)—, —C($R_7$)$_2$—, —O— or —S(O)$_n$
$K_{10}$ represents —N($R_{10}$)—, —C($R_{10}$)$_2$—, —O—, —S(O)$_n$ or —CO— in which n is 0, 1 or 2;

at least one of the groups $K_6$ and $K_7$ represents —C($R_6$)=, —C($R_6$)$_2$—, —C($R_7$)= or —C($R_7$)$_2$— and the divalent radicals —$K_6$—$K_7$—$K_8$—$K_9$— and —$K_6$—$K_7$—$K_{10}$— only contain in their principal chain 0, 1 or 2 nitrogen, oxygen or sulphur atoms and no —O—O— or —S—S— linkage (preferably —$K_6$—$K_7$—$K_8$—$K_9$— forms an aromatic ring), and in which:

$R_6$, $R_7$, $R_8$, $R_9$ or $R_{10}$, which are identical or different, each represents:

hydrogen or halogen, at least one of $R_6$ and $R_7$ being other than hydrogen, cyano, nitro, thiocyanato, hydroxyl or carboxyl, alkyl, cycloalkyl, alkenyl, alkynyl, alkyl-S(O)$_n$ (in which n=0, 1 or 2), alkoxy, cycloalkoxy, alkenyloxy or alkynyloxy (these radicals advantageously contain up to 8 carbon atoms and are optionally substituted by one or more halogen atoms), phenyl, naphthyl, phenyl-S(O)$_n$ (in which n=0, 1 or 2), phenoxy, phenylalkyl (lower alkyl), phenylalkyl-S(O)$_n$ (lower alkyl; n=0, 1 or 2), phenylalkoxy (lower alkoxy) or a 5- or 6-membered, saturated or unsaturated, optionally substituted heterocyclyl containing 1 to 3 oxygen, sulphur or nitrogen atoms, the phenyl or heterocyclyl ring being unsubstituted or substituted by halogen;

nitro, cyano, carboxyl, hydroxyl, mercapto, thiocyanato, (lower) alkoxy-carbonyl, —CO—NR'R", NR'R", —N(R')—CO—R", —O—CO—R' or —O—CO—NR'—R";

lower alkyl, lower alkoxy, (lower) alkyl-S(O)$_n$ (in which n=0, 1 or 2), cycloalkyl (of 3 to 7 carbon atoms), phenyl, phenoxy, phenyl-S(O)$_n$ (in which n=0, 1 or 2), phenylalkyl, phenylalkoxy or phenylalkyl-S (O)$_n$ (in which n=0, 1 or 2), which is optionally halogenated and has 1 to 4 carbon atoms in the alkyl portion; or (lower) alkoxy-carbonyl, CO—NR'R", NR'R", N(R')—CO—R", O—CO—R' or O—CO—NR'R" in which R' and R" which are identical or different, each represents hydrogen lower alkyl; cycloalkyl of 3 to 7 carbon atoms; optionally halogenated phenyl; optionally halogenated phenylalkyl (lower alkyl); alkenyl or alkynyl of 3 to 7 carbon atoms; or alkoxyalkyl of 3 to 8 carbon atoms;

when $K_6$ and $K_7$ represent —C($R_6$)=, —C($R_6$)$_2$—, —C($R_7$)= or —C($R_7$)$_2$—, $R_6$ and $R_7$, or one of the groups $R_6$ together with one of the groups $R_7$, can form, with the carbon atoms to which they are attached a carbon-containing, optionally heterocyclic, 5 or 6 membered ring, which is saturated or unsaturated, and contains 0, 1 or 2 non-adjacent oxygen, nitrogen or sulphur atoms;

when $K_6$, $K_7$, $K_8$, $K_9$ or $K_{10}$ represents a group —N($R_6$)—, —N($R_7$)—, —N($R_8$)—, —N($R_9$)— or —N($R_{10}$)—, then the group $R_6$, $R_7$, $R_8$, $R_9$ or $R_{10}$ represents hydrogen; alkyl of 1 to 6 carbon atoms; phenyl or phenylalkyl (lower alkyl) optionally substituted by one or more halogen atoms or by cyano or nitro or by lower alkyl or lower alkoxy (provided that one at least of $R_6$ and $R_7$ is other than hydrogen).

The compounds of formula (Ia) and (Ib) constitute preferred features of the invention.

Among the compounds of formula (I), (Ia) and (Ib) different and specific sub-families are preferred in particular in view of their properties and their accessibility. These sub-families are defined hereinafter in particular by means of formulae (II), (III), (IV), (V), (VI) and (VII).

Preferred values of the various symbols defined above apply equally hereinafter in particular in relation to the compounds which are useful for combatting fungal attack on plants, it is preferred to use the compounds having a value of log P as defined above.

A first, preferred sub-family of compounds according to the invention comprises the compounds of formula (II) in which:

$K_{110}$ is oxygen, $S(O)_{n1}$ (in which $n_1$ is zero, 1 or 2), $NR_{110}$, $C(R_{110})_2$ or oxo;

$Z_1$ is halogen or $OW_1$ (in which $W_1$ has one of the meanings given for W') or $NHR_{11}$ or $NR_{11}R_{12}$, in which $R_{11}$ and $R_{12}$, which are identical or different, have one of the meanings given, respectively, for $R_1$ and $R_2$;

$R_{13}$ to $R_{15}$, which are identical or different, have one of the meanings given for $R_3$, $R_4$ and $R_5$; ($R_{13}$ and $R_{14}$ preferably together form a methylenedioxy or ethylenedioxy group, the carbon atoms of which are optionally substituted by lower alkyl or halogen);

$R_{16}$ to $R_{19}$, which are identical or different, have one of the meanings given for $R_6$ to $R_9$, when $K_{110}$ is $=C(R_{110})$— or $—C(R_{110})_2$—, then $R_{110}$ represents hydrogen or lower alkyl or benzyl, hydroxyl, lower alkanoyloxy (for example acetyloxy) or lower alkoxy, when $K_{110}$ is $—N(R_{110})$—, then $R_{110}$ represents hydrogen, lower alkyl or benzyl;

When $Z_1$ is an $NR_{11}R_{12}$ group, the compounds have the formula (II') and when $Z_1$ is an $OW_1$ group, the derivatives have the formula (II")

Preferred compounds are those in which:

$K_{110}$ is oxygen, sulphur $—N(R_{110})$— or $—C(R_{110})_2$—, $Z_1$ is a group $OW_1$ as defined above or an $NHR_{11}$ or $NR_{11}R_{12}$ group in which $R_{11}$ and $R_{12}$ are lower alkyl and $R_{11}$ and $R_{12}$ contain at most six carbons in total, or $R_{11}$ and $R_{12}$ together with the nitrogen atom to which they are attached form a morpholino or thiomorpholino group, $R_{13}$ to $R_{15}$ have the same meaning as $R_3$, $R_4$ and $R_5$.

Particularly preferred compounds of formula (II) are those in which:

$Z_1$ is an $OW_1$ group as defined above, or an $NR_{11}R_{12}$ group which is a morpholino, thiomorpholino, N-methyl-N-ethylamino or N,N-diethylamino group, $R_{13}$ to $R_{15}$, which arm identical or different, are hydrogen, halogen, lower alkyl, lower alkoxy or lower alkylthio;

$R_{16}$, $R_{18}$ and $R_{19}$ are hydrogen or fluorine, $R_{17}$ is hydrogen or halogen; lower alkyl, lower alkoxy, lower alkylthio, lower halogenoalkyl, lower halogenoalkoxy or lower halogenoalkylthio; nitro or cyano; lower alkenyl, lower alkynyl or (lower) alkoxy-carbonyl.

Among the compounds of formula (I) a second preferred sub-family comprises the phenylamides of formula (III) in which:

$Z_2$ represents:

halogen;

an $OW_2$ group (in which $W_2$ has one of the meanings given for W'), or an $NHR_{21}$ group, or an $NR_{21}R_{22}$ group in which $R_{21}$ and $R_{22}$, which are identical or different, have one of the meanings given, respectively, for $R_1$ and $R_2$;

$R_{23}$ to $R_{25}$, which are identical or different, have one of the meanings given, respectively, for $R_3$, $R_4$ and $R_5$; $R_{23}$ and $R_{24}$ preferably together form a methylenedioxy or ethylenedioxy group, the carbon atoms of which are optionally substituted by lower alkyl or halogen;

$R_{26}$ and $R_{27}$, which are identical or different, have one of the meanings given, respectively, for $R_6$ and $R_7$, provided that $R_{26}$ and $R_{27}$ are not simultaneously hydrogen;

$R_{28}$ and $R_{29}$, which are identical or different, each represents hydrogen or halogen; hydroxyl; lower alkyl radical; lower alkoxy; (lower) alkoxy- (lower) alkyl; or (lower) alkoxycarbonyl.

Preferred compounds of formula (III), are those in which:

$Z_2$ is a group $OW_2$ (in which $W_2$ has one of the meanings given for W') or an $NHR_{21}$ group or an $NR_{21}R_{22}$ group, in which $R_{21}$ and $R_{22}$ are lower alkyl and $R_{21}$ and $R_{22}$ contain at most six carbons in total, or $R_{21}$ and $R_{22}$, together with the nitrogen atom to which they are attached, form a morpholino or thiomorpholino group;

$R_{23}$ to $R_{25}$, which are identical or different, have the same meaning as $R_3$, $R_4$ and $R_5$;

$R_{28}$ and $R_{29}$, which are identical or different, each represents hydrogen, halogen or hydroxyl.

Particularly preferred compounds of formula (III) are those in which:

$Z_2$ is an $OW_2$ group as defined above or an $NR_{21}R_{22}$ group which is a morpholino, thiomorpholino, N-methyl-N-ethylamino or N,N-diethylamino group;

$R_{23}$ to $R_{25}$, which are identical or different, each represents hydrogen or halogen, lower alkyl, lower alkoxy or lower alkylthio;

$R_{26}$ and $R_{27}$, which are identical or different, each represents hydrogen or halogen, lower alkyl, lower alkenyl, lower alkoxy, lower alkylthio, lower halogenoalkyl, lower halogenoalkoxy or lower halogenoalkylthio;

$R_{28}$ and $R_{29}$, which are identical or different, each represents hydrogen or fluorine.

Among the compounds of formula (I) a third preferred sub-family comprises the nicotinic acid derivatives of formula (IV) in which:

$Z_3$ represents:

halogen, or an $OW_3$ group (in which $W_3$ has one of the meanings given for W') or an $NHR_{31}$ group or an $NR_{31}R_{32}$ group, in which $R_{31}$ and $R_{32}$, which are identical or different, have one of the meanings given, respectively, for $R_1$ and $R_2$, $R_{33}$ to $R_{35}$, which are identical or different, have one of the meanings given, respectively, for $R_3$, $R_4$ and $R_5$; $R_{33}$ and $R_{34}$ preferably together form a methylenedioxy or ethylenedioxy group, the carbon atoms of which are optionally substituted by lower alkyl or halogen;

$R_{37}$ has one of the meanings given for $R_7$, provided that $R_7$ is not hydrogen;

$R_{38}$ and $R_{39}$, which are identical or different, each represents hydrogen or halogen, lower alkyl, lower alkoxy, (lower) alkoxy-(lower) alkyl or lower alkoxycarbonyl or a cyano group: and when $R_{37}$ is phenyl, $R_{38}$ can form, with the carbon atom of $R_{37}$ which is in the ortho position to that linked to the pyridine ring, a chain $Y_3$-$(CH_2)_{n3}$, in which $Y_3$ is oxygen, sulphur or a methylene group, and $n_3$ is 0, 1 or 2.

Compounds of formula (IV) in which $R_{33}$ to $R_{35}$, which are identical or different, each represents hydrogen, halogen (one at least of $R_{33}$, $R_{34}$ and $R_{35}$ being other than hydrogen or halogen), or lower alkyl, lower alkoxy or lower alkylthio.

Among the compounds of formula (I) a fourth preferred sub-family comprises the derivatives of formula (V) in which:

$Z_4$ represents:

halogen, or an $OW_4$ group (in which $W_4$ has one of the meanings given for W'), an $NHR_{41}$ group or an $NR_{41}R_{42}$ group in which $R_{41}$ and $R_{42}$, which are identical or different, have one of the meanings given, respectively, for $R_1$ and $R_2$;

$R_{43}$, $R_{44}$ and $R_{45}$, which are identical or different, have one of the meanings given, respectively, for $R_3$, $R_4$ and $R_5$;

$R_{47}$ has one of the meanings given for $R_7$, but is other than hydrogen;

$R_{49}$ represents hydrogen or lower alkyl.

Preferred compounds of formula (V) are those in which:

$Z_4$ is $OW_4$ (in which $W_4$ has one of the meanings given for W'), an $NHR_{41}$ group or an $NR_{41}R_{42}$ group, in which $R_{41}$ and $R_{42}$ are lower alkyl groups such that $R_{41}$ and $R_{42}$ are lower alkyl groups such that $R_{41}$ and $R_{42}$ contain at most six carbons in total, or $R_{41}$ and $R_{42}$ together, with the nitrogen atom to which they are attached, form a morpholino or thiomorpholino group;

$R_{43}$ to $R_{45}$, which are identical or different, each represents hydrogen or halogen, lower alkyl, lower alkoxy or lower alkylthio;

$R_{49}$ is hydrogen.

A preferred fifth sub-family of compounds within formula (I) comprises the compounds of formula (VI) in which:

$Z_5$ represents a halogen atom or an $OW_5$ group (in which $W_5$ has one of the meanings given for W') or an $NHR_{51}$ group or an $NR_{51}R_{52}$ group in which $R_{51}$ and $R_{52}$, which are identical or different, have one of the meanings given, respectively, for $R_1$ and $R_2$;

$R_{53}$, $R_{54}$ and $R_{55}$, which are identical or different, have one of the meanings given, respectively, for $R_3$, $R_4$ and $R_5$; $R_{53}$ and $R_{54}$ preferably together form a methylenedioxy or ethylenedioxy group, the carbon atoms of which are optionally substituted by lower alkyl or halogen;

$R_{56}$ and $R_{57}$ have one of the meanings given for $R_6$ and $R_7$, provided that $R_6$ and $R_7$ are not simultaneously hydrogen;

$R_{59}$ represents hydrogen, halogen or hydroxyl; or optionally halogenated lower alkyl, lower alkoxy or lower alkoxyalkyl.

Preferred compounds of formula (VI) are those in which $R_{53}$ to $R_{55}$, which are identical or different, are hydrogen, halogen, lower alkyl, lower alkoxy or lower alkylthio; and $R_{59}$ is a hydrogen atom or a lower alkyl group.

A sixth preferred sub-family of compounds according to general formula (I) comprises the compounds of formula (VII) in which:

$Z_6$ represents:

halogen;

an $OW_6$ group (in which $W_6$ has one of the meanings given for W'), an $NHR_{61}$ group or an $NR_{61}R_{62}$ group in which $R_{61}$ and $R_{62}$, which are identical or different, have one of the meanings given, respectively, for $R_1$ and $R_2$;

$K_{66}$ is $-N(R_{66})-$, $-N=$, sulphur, oxygen or $=C(R_{66})-$, $K_{67}$ is sulphur, oxygen, $-N(R_{67})-$, $-N=$, or $=C(R_{67})-$, it being understood that $K_{66}$ and $K_{67}$ cannot simultaneously be $-N(R_{66})-$ and $-N(R_{67})-$;

$K_{610}$ is $-N(R_{610})-$, $-N=$, sulphur, oxygen, or $=C(R_{610})-$, it being understood that $K_{610}$ and $K_{67}$ cannot simultaneously be $-N(R_{610})-$ and $-N(R_{67})-$;

$R_{63}$, $R_{64}$ and $R_{65}$, which are identical or different, have one of the meanings given, respectively, for $R_3$, $R_4$ and $R_5$;

$R_{66}$, $R_{67}$ and $R_{610}$, which are identical or different, have one of the meanings given, respectively, for $R_6$, $R_7$ and $R_{10}$.

Preferred derivatives of formula VII, are those in which:

$Z_6$ is an $OW_6$ radical (in which $W_6$ has one of the meanings given for W'), an $NHR_{61}$ group or an $NR_{61}R_{62}$ group in which $R_{61}$ and $R_{62}$ contain at most six carbon atoms in total or $R_{61}$, and $R_{62}$ together with the nitrogen atom to which they are attached form a morpholino or thiomorpholino group;

$K_{66}$ is $-N(R_{66})-$;

$K_{67}$ is $-N=$ or $=C(R_{67})-$;

$K_{610}$ is $=CH-$;

$R_{63}$, $R_{64}$ and $R_{65}$, which are identical or different, each represents hydrogen, halogen, lower alkyl, lower alkoxy or lower alkylthio;

$R_{66}$ and $R_{67}$, which are identical or different, each represents hydrogen, or an alkyl, phenyl or phenylalkyl group, optionally substituted by halogen or halogenoalkyl, it being understood that $R_{66}$ and $R_{67}$ cannot simultaneously be hydrogen.

The compounds of the invention are useful, because of their remarkable fungicidal properties, in particular, in agriculture, and also as synthetic intermediates in particular for the preparation of other compounds of formula (I).

Preferred compounds of the invention with the exclusion of the following compounds of formula (Ia) and (Ib):

the compounds of formula (Ia) in which Y is oxygen, and at the same time $K_8$ and $K_9$ are either $-CH=$, or one is $-N=$ and the other $-CH=$, and at the same time $K_6$ and $K_7$ together form an unsaturated carbon-containing ring joined to the 5-membered ring comprising $K_{10}$;

the compounds of formula (Ib) in which Y is oxygen, and at the same time $K_{10}$ is O, S, SO, $SO_2$, $NR_{10}$ ($R_{10}$ having the meaning given above), $CH_2$ or CO, and at the same time $K_6$ and $K_7$ together form an unsaturated carbon-containing ring joined to the 5-membered ring comprising $K_{10}$.

PREPARATION PROCESSES

The derivatives according to the invention can be prepared according to several processes.

The preparation of compounds of formula (II) is described below.

According to a first process (process A) which is particularly suitable for the compounds of formula (II) in which $K_{110}$ is $-O-$, $-S-$ or $NHR_{110}$, the starting point is a benzophenone of formula (XII') in which $R_{13}$ to $R_{19}$ have the same meanings as above (including the preferred meanings) and $A_1$ is a substitutable halogen atom (such as bromine or, preferably, chlorine or fluorine) or a nitro group, which is reacted with a derivative of formula:

$H-K_{110}-CH_2-CO-Z_1$ in which $K_{110}$ and $Z_1$ have the same meaning as above, to give a derivative of formula (II) by replacement of $A_1$ and cyclization.

This reaction is advantageously carried out in an alcoholic solvent (lower alkanol for example) in the presence of the corresponding alkanolate (for example $CH_3ON_a$, $C_2H_5ON_a$ or $C_3H_7ON_a$) or in the presence of an organic base such as an amine, preferably a tertiary amine (triethylamine), or an inorganic base such as the hydroxides, carbonates or hydrogenocarbonates, this base being derived from the alkali or alkaline-earth metals such as, for example, sodium, potassium or calcium.

The reaction can also be carried out in the presence of the same bases in an aprotic dipolar solvent such as dimethylsulphoxide, dimethylformamide, N,N-dimethylacetamide, N-methylpyrrolidone or hexamethylphosphotriamide.

In the case of derivatives of formula (II") the latter can be converted (process G) to derivatives of formula (II') by heating, to a temperature of between 100° C. and 200° C. and optionally under pressure, with an excess of amine $HNR_{11}R_{12}$ according to the outline:

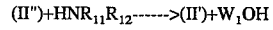
(II")+$HNR_{11}R_{12}$------>(II')+$W_1OH$

When, in formula (II"), $W_1$ is a hydrogen atom, these derivatives must first of all undergo activation of the acid function by an agent such as thionyl chloride (SOCl$_2$), phosphoryl chloride (POCl$_3$), phosphorus trichloride or phosphorus pentachloride (PCl$_3$, PCl$_5$), dicyclohexylcarbodiimide, carbonyldiimidazole, ethyl chloroformate or trifluoroacetic anhydride, before treatment with the amine HNR$_{11}$R$_{12}$ at a temperature of between 0° C. and 50° C. in a solvent such an THF (tetrahydrofuran) or a chlorinated solvent (in particular an aliphatic or aromatic hydrocarbon), preferably in the presence of an excess of amine HNR$_{11}$R$_{12}$ or in the presence of an inorganic or organic base such as triethylamine.

It is possible to prepare other derivatives of formula (II') from derivatives of formula (II') by the conventional techniques of functional group conversion of organic chemistry.

For example, in the case in which a nitrated derivative (formula (II) in which $R_{16}$ or $R_{17}$ or $R_{18}$ or $R_{19}$ is NO$_2$) is obtained, it can be reduced (process B) to an amine derivative by a reducer such as a metal (iron, tin) or a salt of these metals (tin chloride) in an inorganic (HCl, H$_2$SO$_4$) or organic (ethyl alcohol or a carboxylic acid, in particular acetic acid) acid medium. As reducer, hydrogen (optionally under pressure) or its precursors (sodium borohydride, formic acid derivatives, cyclohexene) can also be used in the presence of a transition metal such as palladium. In this case, ethyl acetate, acetic acid or an alcohol such as ethyl alcohol is advantageously used as solvent.

The amine derivative obtained (formula (II) in which $R_{16}$ or $R_{17}$ or $R_{18}$ or $R_{19}$ are NH$_2$) can itself be subjected to acylation reactions (process C) or diazotation reactions. The acylation reaction is carried out with the aid of carboxylic acid derivatives (acid chloride or acid anhydride) in the presence of an organic (triethylamine, pyridine) or inorganic (hydroxide, carbonate or hydrogen carbonate of alkali metals) base in an aprotic solvent such as a chlorinated solvent (methylene chloride, chloroform) or an aromatic solvent (benzene, toluene) or an aliphatic ether (diethyloxide, tetrahydrofuran, 1,2-dimethoxyethane).

Diazotation (process D) is carried out by treating a solution of the amine derivative (formula (II) in which $R_{16}$ or $R_{17}$ or $R_{18}$ or $R_{19}$ are NH$_2$) in a strong inorganic acid (hydrochloric, hydrobromic or sulphuric acid), with an alkali nitrite (sodium nitrite), at a temperature of between −10° C. and +15° C. The diazonium salt thus obtained is then decomposed at temperatures of between +5° C. and +100° C. in the presence of different agents such as cuprous chloride, cuprous bromide, potassium iodide, cuprous oxide or potassium ethylthioxanthate to give, respectively, derivatives in which the amino group has been replaced by an atom of chlorine, an atom of bromine, an atom or iodine, a hydroxyl group or a mercapto group.

In the case in which a bromine atom is introduced, an aryl coupling reaction can be carried out (process E) with a boronic acid R$_{17}$B(OH)$_2$ in which $R_{17}$ can be a heterocycle or a phenyl or a vinyl group (these groups can be substituted as indicated in the definition of $R_7$) to lead to other derivatives according to the invention.

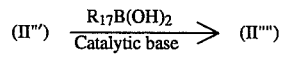

The reaction takes place just as well when $Z_1$=OW$_1$ (W2=H or alkyl, or alkali metal) as when $Z_1$=NR$_{11}$R$_{12}$.

Commercial palladium complexes Pd [P(C$_6$H$_5$)$_3$]$_4$, palladium tetrakis(triphenylphosphine) or complexes prepared in situ from a palladium salt such an palladium acetate and a phosphine such as triphenylphosphine or tri-o-tolylphosphine can be used as catalyst. An inorganic base such as the carbonates and hydrogen carbonates of alkali metals (Na$_2$CO$_3$, NaHCO$_3$ and the like) or an organic base such as an amine (triethylamine) can be used as base. The reaction takes place with an inorganic base in a heterogeneous medium comprising an organic phase which can be a hydrocarbon solvent such as benzene or toluene or an ether with a high boiling point such as glyme or its higher derivatives diglyme or triglyme, and a basic aqueous phase. The reaction can also take place with an organic base in a homogeneous medium in the presence of a solvent such as dimethylformamide or N-methylpyrrolidone. The boronic acids used can be commercial compounds, or can be prepared by the interaction of an organometallic derivative R$_{17}$M$_1$, in which $R_{17}$ has the same meaning as above, (M$_1$=Li or MgX with X=Cl or Br) with an alkyl borate B(OR)$_3$, (with R'=CH$_3$, C$_2$H$_5$, C$_3$H$_7$, i-C$_3$H$_7$ or C$_4$H$_9$) followed by an acid hydrolysis according to the operating methods described in Organic Synthesis coll. vol. 4 page 68 or in Journal of Organic Chemistry 49 pages 5237–5243 (1984). The reagents are used in the following proportions:

Boronic acid R$_{17}$B(OH)$_2$:1.05 to 1.50 equivalents
Base:4.00 to 6.00 equivalents
Catalyst:0.005 to 0.03 equivalents
Substrate of formula II''':1.00 equivalent The reaction takes place at a temperature of between 50° C. and 150° C., preferably at the reflux temperature of the reaction mixture, for a time ranging from two to forty eight hours. The derivative of formula (II''') is isolated by the normal methods; extraction or precipitation by addition of water to the reaction mixture, and can be purified by recrystallization or chromatography in an appropriate solvent.

In another process (process F), which is a variant of process D, a compound of formula (II), in which one of the substituents $R_{16}$ to $R_{19}$ is an unsubstituted amino group and $Z_1$ and $R_{13}$ to $R_{15}$ have the meaning already indicated is reacted (hot, at a temperature of between 40° C. and the boiling point of the solvent) with a lower alkyl nitrite such as t-butyl nitrite, in a solvent such as totrahydrofuran or dimethylformamide to obtain a derivative of formula (II) in which the amino group is replaced by a hydrogen atom, and where $Z_1$ and $R_{13}$ to $R_{19}$ have the meaning already indicated.

The derivatives of formula (XII') can be prepared by a Friedel-Crafts reaction according to the outline:

(XII''')+(XII'')------>(XII')

in which A$_1$ and R$_{13}$ to R$_{19}$ have the same meaning an above, compounds (XII''') and (XII'') being known per se.

This reaction in carried out in the presence of a Lewis acid in a catalytic or stoichiometric quantity (FeCl$_3$, AlCl$_3$, ZnCl$_2$, SnCl$_4$) in the presence or absence of a solvent (nitrobenzene, aliphatic chlorinated solvents or carbon dioulphide). The reaction is carried out between −10° C. and 200° C. according to the experimental conditions used.

According to another process (process G) which is particularly suitable for the compounds of formula (II) in which $K_{110}$ is a C(R$_{110}$)$_2$ group and where $R_{13}$ to $R_{19}$ have the same meanings as above (including for the preferred meanings), a benzophenone of formula (XXII') in which $Z_{11}$=OH and $R_{13}$ to $R_{19}$ have the same meanings as above (including for the preferred meanings) is reacted with thionyl chloride (SOCl$_2$), phosphoryl chloride (POCl$_3$), phosphorus trichloride or phosphorus pentachloride ($PCl_3$ or $PCl_5$) to obtain a benzophenone of formula (XXII') in which $Z_1=Cl$ and $R_{13}$ to $R_{19}$ have the same meanings an above.

In a general manner, the compound thus obtained can not be isolated; it is put to react with a lower alkyl malonate in the presence of a base, which is preferentially a magnesium alkanoate, such as magnesium ethylate. The compound of formula (XXII") in which $W_1$ is a lower alkyl, thus obtained is then treated with a base such as an alkali metal or alkaline-earth metal alkanoate or an inorganic base such as the hydroxides and carbonates of alkali metals in an aqueous or alcoholic medium or in an aprotic dipolar solvent such as dimethylsulphoxide, dimethylformamide or N-methylpyrrolidone, to give a compound of formula (II) in which $K_{110}$ is an oxo group and where $R_{13}$ to $R_{19}$ have the same meanings as above and $Z_1$ is an $OW_1$ group where $W_1$ is a lower alkyl.

This compound, treated hot at a temperature of between 100° C. and 200° C., optionally under pressure, with an excess of an amine $HNR_{11}R_{12}$ in the presence or absence of a solvent, provides a compound of formula (II) in which $K_{110}$ is an oxo group and where $R_{13}$ to $R_{19}$ have the same meaning as above and $Z_1$ is an $NR_{11}R_{12}$ group such as defined. This last compound can be reduced by an appropriate reducer, such as sodium borohydride, in the presence of cerium trichloride in an alkanol such as ethanol, to provide a compound of formula (II) in which $K_{110}$ is a CH(OH) group and $Z_1$ is an $NR_{11}R_{12}$ group such an defined.

These two latter products can undergo the conventional reactions of organic chemistry (addition of an organometallic compound for the first, acylation or alkylation for the second) to provide other derivatives of formula (II).

According to another process (process H) which is particularly suitable for the compounds of formula (II) in which $K_{110}$ is a $C(R_{110})_2$ group and where $R_{13}$ to $R_{19}$ have the same meanings as above (including the preferred meanings), a derivative of formula (XXXII'), in which $Z_1$ is an $OW_1$ or $NR_1R_2$ group is reacted with a benzyl halide of formula (XXXII') where $R_{16}$ to $R_{110}$ have the same meaning as above and where Hal designates a halogen atom, such as chlorine or bromine. The reaction takes place in the presence of a base, which is preferably an alkali metal or alkaline-earth metal alkanoate, or in the presence of an inorganic base such as the hydroxides of alkali metals, in an alkanol medium, or in an aprotic dipolar solvent such as dimethylsulphoxide, dimethylformamide or N-methylpyrrolidone, to provide a compound of formula (XXXII''') in which $R_{13}$ to $R_{19}$ and $Z_1$ have the preceding meanings. This compound, treated with an organic or inorganic acid, preferably polyphosphoric acid, in the presence or absence of a solvent (toluene, xylene) at a temperature of between 0° C. and 150° C., provides a derivative of formula (II) in which $K_{110}$ is a $C(R_{110})_2$ group and $R_{13}$ to $R_{19}$ have the preceding meaning. If the derivative $Z_1=OW_1$ is obtained, with $W_1$ a lower alkyl or the hydrogen atom, it can be converted to the derivative where $Z_1=NR_1R_2$ by the conventional techniques of organic chemistry indicated in the first process.

According to another process (process I, that is to say capital i) which is particularly suitable for the compounds of formula (II) in which $K_{110}$ is a $C(R_{110})_2$ group and where $R_{13}$ to $R_{19}$ have the same meanings as above (including the preferred meanings), a derivative of formula (XXXII') in which $Z_1$ is an $OW_1$ or $NR_{11}R_{12}$ group is reacted with a benzaldehyde substituted by radicals $R_{16}$, $R_{17}$, $R_{18}$ or $R_{19}$. The reaction takes place in a solvent which can be an aromatic hydrocarbon or a carboxylic acid, in the presence of a catalyst which is preferentially a disubstituted amine such as piperidine; a compound of formula (XXXXII') is thus obtained in which the groups $R_{13}$ to $R_{19}$ and $Z_1$ have the same meanings as above. This compound is then reduced with an appropriate reducer, such as the sodium borohydride in the presence of cerium chloride described above in the second process. The allyl alcohol obtained is cyclized by treatment with an organic or inorganic acid in a quantity which in catalytic or greater than stoichiometry, in the presence or absence of a solvent (toluene, xylene) at a temperature of between 0° C. and 150° C., to provide a derivative of formula (II) in which $K_{110}$ is a $CH_2$ group and $R_{13}$ to $R_{19}$ have the preceding meaning. If the derivative $Z_1=OW_1$ is obtained, with $W_1$ a lower alkyl or the hydrogen atom, it can be converted to $Z_1=NR_1R_2$ by the conventional techniques of organic chemistry indicated in the first process.

The preparation of compounds of formula (III) is described below:

The preparation of compounds of formula (III) is carried out, according to a process which is also part of the invention, by an aryl coupling reaction between a boronic acid $R_{27}B(OH)_2$ [in which $R_{27}$ can be a heterocycle, a phenyl or a vinyl group (these groups being capable of being substituted as indicated in the definition of $R_7$)] and a brominated derivative of formula (XIII'), it being understood that none of the other substituents can simultaneously be a bromine or iodine atom. The outline of the reaction of this aryl coupling is:

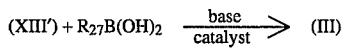

The reaction takes place just as well with $Z_2=OW_2$ ($W_2$=H or alkyl, or alkali metal) as with $Z_2=NR_{21}R_{22}$.

Commercial palladium complexes Pd $[P(C_6H_5)_3]_4$, palladium tetrakis(triphenylphosphine) or complexes prepared in situ from a palladium salt such as palladium acetate and a phosphine such an triphenylphosphine or tri-o-tolylphosphine can be used as catalyst. An inorganic base such as the carbonates and hydrogen carbonates of alkali metals ($Na_2CO_3$, $NaHCO_3$ and the like) or an organic base such as an amine (triethylamine) can be used as base. The reaction takes place with an organic base in a heterogeneous medium comprising an organic phase which can be a hydrocarbon solvent such as benzene or toluene or an ether with a high boiling point such as glyme or its higher derivatives diglyme or triglyme, and a basic aqueous phase. The reaction can also take place with an organic base in a homogeneous medium in the presence of a solvent such as dimethylformamide or N-methylpyrrolidone. The boronic acids used can be commercial compounds, or can be prepared by the interaction of an organometallic derivative $R_{27}M_2$, in which $R_{27}$ has the same meaning as above, ($M_2$=Li or MgX with X=Cl or Br) with an alkyl borate $B(OR)_3$, (with $R'=CH_3$, $C_2H_5$, $C_3H_7$, i-$C_3H_7$ or $C_4H_9$) followed by an acid hydrolysis according to the operating methods described in Organic Synthesis coll. vol. 4 page 68 or in Journal of Organic Chemistry 49 pages 5237–5243 (1984). The reagents are used in the following proportions:

Boronic acid $R_{27}B(OH)_2$:1.05 to 1.50 equivalents
Base:4.00 to 6.00 equivalents
Catalyst:0.005 to 0.03 equivalents
Substrate of formula XIII':1.00 equivalent The reaction taken place at a temperature of between 50° C. and 150° C. preferably at the reflux temperature of the reaction mixture, for a time ranging from two to forty eight hours. The derivative of formula (III) is isolated by the normal methods, extraction or precipitation by addition of water to the reaction mixture, and can be purified by recrystallization or chromatography in an appropriate solvent.

The brominated derivative of formula (XIII') can be obtained by diazotation of the amine of formula (XIII")

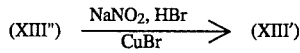

The reaction takes place just as well with the derivatives in the formula of which $Z_2=OW_2$ ($W_2=H$ or alkyl) as with the derivatives in the formula of which $Z_2=NR_{21}R_{22}$. The reaction is carried out by treating a solution of the amine derivative (XIII') in a strong inorganic acid (sulphuric or hydrobromic acid) optionally containing an organic acid (acetic acid) with an alkali nitrite (sodium nitrite) at a temperature of between $-10°$ C. and $+10°$ C. The diazonium salt thus obtained is then decomposed at temperatures of between $+5°$ C. and $+90°$ C., in the presence of hydrobromic acid and cuprous bromide.

The product of formula (XIII') is isolated by the normal methods, extraction or precipitation by the addition of water to the reaction mixture, and can be purified by recrystallization or chromatography in an appropriate solvent.

The amine (XIII") is obtained by an aryl coupling reaction between the phenylboronic acid of formula ($A_2$) which is suitably substituted by $R_{23}$, $R_{24}$, $R_{25}$ and a halogenated (brominated or iodinated) derivative of formula (XIII"') according to the outline:

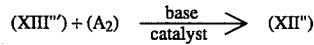

in which formulae the radicals $Z_2$, $R_{26}$, $R_{28}$ and $R_{29}$, with the reservation that $R_{26}$, $R_{28}$ and $R_{29}$ are not simultaneously a bromine or iodine atom, have the same meaning as those indicated above, and Hal represents a halogen atom, in particular bromine or iodine.

The reaction takes place just an well with $Z_2=OW_2$ ($W_2=H$, or alkyl/or alkali metal) as with $Z_2=NR_{21}R_{22}$. The reaction conditions are identical to those described above for conversion from (XIII') to (III).

The amine (XIII"') can be obtained by reduction of a nitrated derivative of formula (XIII"").

The reaction takes place just an well with the derivatives in the formula of which $Z_2=OW_2$ ($W_2=H$, or alkyl) as with the derivatives in the formula of which $Z_2=NR_{21}R_{22}$. As a reducer, a metal, (for example: iron, tin) or a salt of these metals (for example: tin chloride) can be used in an inorganic (HCl, $H_2SO_4$) or organic (acetic acid) acid medium. Hydrogen (optionally under pressure) or its precursors (sodium borohydride derivatives of formic acid, cyclohexane) can also be used as reducer in the presence of a transition metal such as palladium or platinum. In this case, ethyl acetate, acetic acid or an alcohol such as ethyl alcohol are advantageously used as solvent. The product of formula (XIII"') is isolated by the normal methods: extraction or precipitation by addition of water to the reaction mixture, and can be purified by recrystallization or chromatography in an appropriate solvent. The derivatives of the (XIII"") type are known compounds.

For the compounds of formula (III') and (XIII'), if the derivative in the formula of which $Z_2$ $OW_2$ is obtained, it is possible to convert it into a derivative in the formula of which $Z_2=NR_{21}NR_{22}$ by the conventional techniques of functional group conversion of organic chemistry. Thus, when $Z_2$ is $OW_2$ with $W_2=$alkyl, it is possible to convert it to $Z_2=NR_{21}NR_{22}$ by heating to a temperature of between $100°$ C. and $200°$ C., optionally under pressure, with an excess of an amine $HNR_{21}R_{22}$, according to the following outline:

Compound (III') [compound (III) with a $CO-OW_2$ group] +

$HNR_{21}R_{22}$ ⟶

Compound (III') [compound (III) with a $CO-NR_{21}R_{22}$ group] +

$W_2OH$

From compounds in the formula [(III"), (XIII') or (XIII"")] of which $Z_2=OW_2$ with $W_2=$alkyl, compounds in the formula of which $Z_2=OM_2$ where $M_2$ is an alkali metal, can also be obtained by a saponification reaction with an inorganic base such as alcoholic sodium hydroxide or potassium hydroxide. These compounds, when treated with an inorganic acid such as hydrochloric or sulphuric acid, provide, respectively, derivatives (III), (XIII') or (XIII"") with $Z_2=OH$.

From the derivative in the formula [(III), (XIII') or (XIII"")] of which $Z_2=OH$, the compound in the formula of which $Z_2=NR_{21}R_{22}$ can also be obtained after activation of the carboxylic acid function with an agent such as thionyl chloride ($SOCl_2$), phosphoryl chloride ($POCl_3$), phosphorus trichloride or phosphorus pentachloride ($PCl_3$, $PCl_5$), dicyclohexylcarbodiimide, carbonyl diimidazole, the alkyl chloroformates or trifluoroacetic anhydride, and reaction with the amine $HNR_{21}R_{22}$ in the presence of an organic or inorganic base, in an organic solvent such as a chlorinated or aromatic solvent or an ether such as TMF.

The preparation of compounds of formula (IV) is described below:

The preparation of compounds of formula (IV) can be carried out, for example, by cyclization of a derivative of formula (XIV')

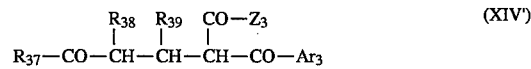

in which $Ar_3$ is a group of formula (XIV"), that is to say a phenyl group substituted by $R_{33}$, $R_{34}$ and $R_{35}$, and $Z_3$, $R_{33}$ to $R_{39}$ have the same meaning as above, hot in the presence of an ammonium donor, in an acid medium.

The intermediate derivatives of formula (XIV') are new compounds which are part of the invention. They can be prepared according to a process in which reaction of a 3-propioketone and a suitably substituted benzoylacetate or acetamide is carried out according to the following outline:

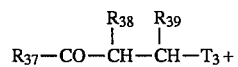

$Z_3-CO-CH_2-CO-Ar_3 \longrightarrow$ (XIV')

in which formulae $Z_3$ and $R_{33}$ to $R_{39}$ have the same meanings as for the formula (XIV') and $T_3$ designates a leaving group such as a halogen atom or a quaternary ammonium group, in the presence of a strong inorganic base and a solvent.

In the case where the $T_3$ group is a quaternary ammonium group, a compound derived from a Mannich base, that is to say a derivative of formula

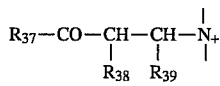

is then reacted with a derivative of formula

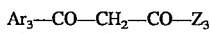

in an alkaline medium, in the presence of a solvent of the alcohol type.

These latter derivatives are known per se.

The derivatives of formula (IV), in which $Z_3$ is the OH group, that is to say the derivatives of formula (IV''') with $W_3=H$, can also be prepared according to a process characterized in that an ester of formula (IV'') in which $W_3$ is a lower alkyl radical, is saponified and then it is acidified.

Finally, it is possible to convert derivatives of formula (IV'') with $W_3$=lower alkyl to the derivatives of formula (IV') in which $Z_3$ in the $NR_{31}R_{32}$ group by saponification, as indicated in the preceding paragraph, then halogenation of these acids to halides of the corresponding acids, and reaction of these halides with an amine of formula $HNR_{31}R_{32}$ in which $R_{31}$ and $R_{32}$ have the meaning indicated above.

The preparation of products of formula (V) in described below:

According to a first process, an enone of formula (XV')

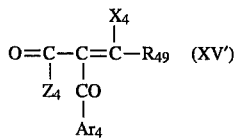

in which $Ar_4$ has the formula (XV'')

$R_{43}$, $R_{44}$, $R_{45}$, $R_{49}$ and $Z_4$ have the same meaning as in formula (V) and $X_4$ is a (lower) dialkyl-amino or (lower) alkoxy group, is reacted with an amidine of formula

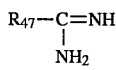

or one of its salts of formula

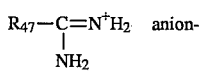

in which $R_{47}$ has the same meaning as above, in the presence of a solvent in a basic medium. This reaction is advantageously carried out in an organic solvent, in particular an alcoholic solvent, for example methanol, ethanol or propanol, in the presence of the corresponding alcoholate or of an organic base such an amine, preferably a tertiary amine, or an inorganic base such as a hydroxide, carbonate or hydrogen carbonate, of an alkali metal or alkaline-earth metal such as, for example, sodium, potassium or calcium. The reaction can also be carried out in water, in the presence of the inorganic bases mentioned above. In the case of derivatives of formula (V'), that is to say of the derivatives of formula (V) in which $Z_4$ is an $NR_{41}R_{42}$ group as defined above, a derivative of formula (V''), that is to say a derivative of formula (V) in which $Z_4$ is an $OW_4$ group as defined above, is reacted with an amine of formula $HNR_{41}R_{42}$ and removal of $W_4OH$. When, in formula (V''), $W_4$ is a hydrogen atom, these derivatives must first of all undergo activation of the acid function by an agent such as dicyclohexylcarbodiimide, carbonyldiimidazole, ethyl chloroformate or trifluoroacetic anhydride, thionyl chloride ($SOCl_2$), phosphoryl chloride ($POCl_3$), phosphorus trichloride or phosphorus pentachloride ($PCl_3$, $PCl_5$) before treatment with the amine $HNR_{41}R_{42}$ in the presence of an organic base in an organic solvent such as a chlorinated or aromatic solvent (in particular a hydrocarbon) or an ether such as THF.

From derivatives of formula (V') it is possible to prepare other derivatives of formula (V') by the conventional techniques of functional group conversion of organic chemistry.

The derivatives of formula (XV') can be prepared according to a process in which a derivative of formula (XV''')

in which $Ar_4$, $R_{43}$, $R_{44}$, and $R_{45}$, and $Z_4$ have the meanings indicated above, is reacted with a derivative of formula (XV'''').

in which $R_{49}$ and $X_4$ have the same meaning as above, and $R_{410}$ is a lower alkyl radical.

According to a second process for preparation of derivatives of formula (V), in the case where $R_{47}$ is not an alkyl- or benzyl-sulphinyl or sulphonyl radical, a derivative of formula (XXV') in which $R_{43}$ to $R_{45}$, $R_{49}$ and $Z_4$ have the meanings indicated above and $A_4$ is a (lower) alkylsulphonyl or benzylsulphonyl group, is reacted with a derivative of formula $R_{47}H$ in which $R_{47}$ is a radical having the same meaning as $R_7$, with the reservation that the valency bond linking it to the hydrogen atom is also bonded in $R_{47}$ to a hetero atom such as O, S or $NR_{47}$.

This reaction takes place in a solvent and alkaline medium, advantageously in a protic or aprotic solvent, in the presence of an organic or inorganic base such as the hydroxides, carbonates or hydrogen carbonates of alkali metals or alkaline-earth metals such as, for example, sodium, potassium or calcium.

Derivatives of formula (XXV') can be prepared by oxidation of a derivative of formula (V) in which $R_{47}$ is a lower alkylthio or benzylthio group, by means of an oxidizing agent such as, for example hydrogen peroxide or peracids such as peracetic acid, metachloroperbenzoic acid or magnesium perphthalate.

The preparation of compounds of formula (VI) is described below.

According to this process, a 2-ethylenephenylketone of formula (XVI') is reacted (Michael's Reaction) with an ester or a β-ketoneamide, of formula $R_{59}$—CO—$CH_2$—$COZ_5$, in which $R_{53}$ to $R_{59}$ and $Z_5$ have the preceding meaning in the presence of an organic or inorganic base, such as, for example partly dehydrated baryta, in a lower alkanol such as ethyl alcohol, and at a temperature of between 0° C. and the boiling point of the solvent used. The compound of formula (XVI") obtained, in the formula of which $R_{53}$ to $R_{59}$ and $Z_5$ have the preceding meaning, can be cyclized by simple heating from 40° C. to the reflux temperature of the solvent in a carboxylic acid medium, preferably in an acetic acid medium, in the presence of a nitrogen donor reagent such as ammonia or an organic or inorganic ammonium salt. A product of formula (VI") or (VI') in thus obtained in which $R_{53}$ to $R_{59}$ have the same meaning as above and with, respectively, $Z_5=OW_5$ and $Z_5=NR_{51}R_{52}$.

If the derivative of formula (VI") is obtained, it can be converted to a derivative of formula (VI') by the conventional techniques of organic chemistry which have already been mentioned in the preceding processes.

The preparation of compounds of formula (VII) is described below.

The compounds according to formula (VII) in which $K_{66}$ is O and $K_{67}$ is —C($R_{67}$)=, and $K_{610}$ is —C($R_{610}$)= are prepared from β,gamma-diketonic esters or amides of formula (XVII') by cyclization in an alcohol or a carboxylic acid, such as acetic acid, by simple heating of the reagent in the presence of a catalytic quantity (0.1 to 5%) of strong acid (inorganic or organic, for example hydrochloric or sulphuric acids) at a temperature of between 40° and 120° C., according to the general method described by Kraff and Daal, Chem. Ber. 21, page 3053 (1888) and repeated by Trebaul and Teste, Bull. Soch. Chim Fr page 2272 (1970).

The compounds according to formula (VII) in which $K_{65}$ is $NR_{66}$, $K_{67}$ is —C($R_{67}$)=, $K_{610}$ is —C($R_{610}$)= are prepared from β,gamma-diketonic eaters or amides of formula (XVII') by hot cyclization in an acid medium in the presence of an amine of formula $NHR_{66}$ in which $R_{66}$ has the preceding meaning. A carboxylic acid such as acetic acid, which also plays the role of catalyst, can be used as solvent. Catalytic quantities of a strong inorganic acid, such as, for example, hydrochloric or sulphuric acid, can also be added. The reaction takes place at a temperature of between 40° C. and the boiling point of the solvent used.

In the case in which the reaction is carried out with ammonia, the product obtained has the formula (VII) in which $K_{66}$ is NH, $K_{67}$ is —C($R_{67}$)=, $K_{610}$ is —C($R_{610}$)=. This compound can be treated with a halogenated derivative $R_{66}$Hal where Hal is a halogen (which can be a chlorine, bromine or iodine atom) in the presence of an inorganic or organic base in a solvent such as dimethylsulphoxide, dimethylformamide or N-methylpyrrolidone to provide a derivative of formula (VII) in which $K_{66}$ is $NR_{66}$, $K_{67}$ is —C($R_{67}$)= and $K_{610}$ is —C($R_{610}$)=.

The diketonic eaters and amides of formula (XVII') can be prepared according to a process in which in that the reaction of a haloketone (optionally substituted by $R_{67}$ and $R_{610}$ radicals) of formula (XVII") with a suitably substituted benzoylacetate or acetamide is carried out according to the following outline:

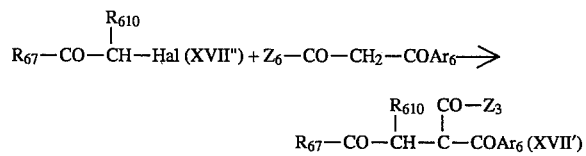

in which $Ar_6$ is a group of formula (XVII'''), that is to say a phenyl group substituted by $R_{63}$, $R_{64}$ and $R_{65}$, in which formulae $Z_6$ and $R_{63}$ to $R_{610}$ have the same meanings as above and Hal designates a leaving group such as a halogen atom.

The compounds according to formula (VII) in which $K_{66}$ is —N= or —N($R_{66}$)— and $K_{67}$ is —N= or N($R_{67}$)—, with the reservation that $K_{66}$ and $K_{67}$ are not simultaneously —N($R_{66}$)— and N($R_{67}$)—, are prepared by the reaction of an enone of formula (XXVII')

in which $Ar_6$ is a group of formula (XVII''') that is to say a phenyl group substituted by $R_{63}$, $R_{64}$ and $R_{65}$; $Z_6$ and $R_{610}$ have the same meaning as above and $X_6$ is a (lower) dialkylamino or alkoxy group with a hydrazine which is optionally substituted by at most one radical $R_{66}$. The reaction takes place in an alkanol such as ethyl alcohol, in the presence of an inorganic or organic base such as triethylamine.

In the case in which $R_{66}$ is a lower alkyl or lower aralkyl group, it is possible to obtain two positional isomers of formula (VII') and (VII") in which, respectively, $K_{66}$ is —N= and $K_{67}$ is —N($R_{67}$)— or $K_{66}$ is —N($R_{66}$)— and $K_{67}$ is —N= the latter being generally in the majority.

The enone used as a starting material is prepared as indicated above in the process for the preparation of compounds of formula (V).

For all the compounds of formula (VII), if the derivative in the formula of which $Z_6=OW_6$ is obtained, it is possible to convert it to the derivative in the formula of which $Z_6=NR_{61}R_{62}$ by the conventional techniques of functional group conversion of organic chemistry. Thus, when $Z_6$ is $OW_6$ with $W_5$=lower alkyl, it is possible to convert it to $Z_6=NR_{61}R_{62}$ by heating to a temperature of between 100° C. and 200° C., optionally under pressure, with an excess of an amine $HNR_{61}R_{62}$.

From the compounds in the formula (VII) of which $Z_6$ is an O-alkyl group, the compounds in the formula of which $Z_6$ is $OM_6$ where $M_6$ is an alkali metal can also be obtained by a saponification reaction with an inorganic base such as alcoholic sodium hydroxide or potassium hydroxide. This compound, treated with an inorganic acid such as hydrochloric or sulphuric acid, provides the derivative (VII) with $Z_6$=OH.

From the derivative in the formula (VII) of which $Z_6$ in OH, the compound in the formula of which $Z_6$ is $NR_{61}R_{62}$ can also be obtained after activation of the carboxylic acid function with an agent such an thionyl chloride ($SOCl_2$), phosphoryl chloride ($POCl_3$), phosphorus trichloride or phosphorus pentachloride ($PCl_3$ $PCl_5$), dicyclohexylcarbodiimide, carbonyldiimidazole, the alkyl chloroformates or trifluoroacetic anhydride, and then a reaction with the amine $HNR_{61}R_{62}$ in the presence of an organic or inorganic base in an organic solvent such as a chlorinated or aromatic solvent (in particular a hydrocarbon) or an ether such as THP.

The following Examples illustrate the invention and show how it can be implemented.

The structure of the various compounds has been confirmed by nuclear magnetic resonance spectrography.

In the Examples, the following abbreviations have been used: m.p. is the melting point expressed in °C. (degrees Celsius). When log P is not given for a product, this means that the product is a chemical intermediate and not a product which is useful against fungal attacks on plants.

Examples 101 to 170 relate to products of the sub-family of formula (II).

EXAMPLE 101

2-(4-Morpholinocarbonyl)5-iodo-3-(3,4-d imethoxyphenyl)benzothiophone—(process D; compound no. 101)

2-(4-Morpholinocarbonyl)5-amino-3-(3,4-dimethoxyphenyl)benzothiophene (1.47 g; 0.0037 mole), distilled water (10 ml) and sulphuric acid concentrated to 98% (1–0 ml) are introduced into a 100 ml flask. While maintaining the temperature of the mixture lower than or equal to 50° C., a solution containing sodium nitrite (0.27 g; 0.0039 mole) in water (5 ml) is progressively poured. Stirring is continued for 1 h, then the reaction mixture is poured into a solution containing water (10 ml) and potassium iodide (0.65 g; 0.0039 mole). The mixture obtained is then progressively heated to 60° C. and maintained at this temperature for 1 hour. After cooling, the reaction mixture is extracted with methylene chloride (3×50 ml); the organic phase is washed with water, dried over magnesium sulphate and evaporated. Purification is carried out by chromatography on silica, and provides 2-(4-morpholinocarbonyl)-5-iodo-3-(3,4-dimethoxyphenyl)benzothiophene (0.9 g) m.p. 214° C. (yield 48%; compound no. 101).

EXAMPLE 102

2-(4-Morpholinocarbonyl)-5-(4-chlorobenzoylamino)-3-(3,4-dimethoxyphenyl)-benzothiophene—(process C; compound no. 102)

2-(4-Morpholinocarbonyl)-5-amino-3-(3,4-dimethoxyphenyl)benzothiophene (2.0 g; 0.005 mole), dichloromethane (50 ml), triethylamine (0.74 ml; 0.0052 mole) and 4-chlorobenzoyl chloride (0.70 ml; 0.0052 mole) are successively introduced into a 100 ml flask.

After stirring at 20° C. for 1 h, the solvent is evaporated, and the solid obtained is rinsed with water, dried in the air and then rinsed with dichloromethane (20 ml ). 2-(4-Morpholinocarbonyl)-5-(4-chlorobenzoylamino)-3-(3,4-dimethoxyphenyl)benzothiophene (1.0 g; 37% ) is thus obtained, m.p. 247° C. (Compound no. 102).

EXAMPLE 103

2-(4-Morpholinocarbonyl)-5-amino-3-(3,4-dimethoxyphenyl)benzothiophene—(process B; compound no. 103)

2-(4-Morpholinocarbonyl)-5-nitro-3-(3,4-dimethoxyphenyl)benzothiophene (10.7 g; 0.025 mole), absolute ethanol (100 ml), concentrated hydrochloric acid (3 ml) and iron powder (4.2 g; 0.075 mole) are successively introduced into a 250 ml flask. The reaction mixture is taken to reflux for two hours and then poured, after cooling, into a saturated solution of sodium bicarbonate (200 ml).

After extraction with ethyl acetate (6×100 ml), the organic phase is dried over magnesium sulphate, filtered and then evaporated to provide 2-(4-morpholinocarbonyl)-5-amino-3-(3,4-dimethoxy-3,4-phenyl)benzothiophene (9.2 g; yield: 92%), m.p. 213° C. (compound no. 103).

EXAMPLE 104

2-(4-Morpholinocarbonyl)-5-nitro-3-(3,4-dimethoxyphenyl)benzothiophene—(process A; compound no. 104)

α-Mercaptoacetomorpholide (9.0 g; 0.0056 mole), potassium carbonate (13.8 g; 0.1 mole), 2-chloro-3'4'-dimethoxy-5-nitrobenzophenone (14.8 g; 0.046 mole) and ethanol (200 ml) are successively introduced into a flask. The mixture is heated to reflux temperature with stirring for two hours, then cooled to ambient temperature and poured into water (1 1); the yellow precipitate which forms is filtered, rinsed with water and then dried under a current of air. 2-(4-Morpholinocarbonyl)-5-nitro-3-(3,4-dimethoxyphenyl)-benzothiophene (18.1 g; 92% ) is thus obtained, m.p. 144.5° C. (compound no. 104).

EXAMPLE 105

2-(4-Morpholinocarbonyl)-5-(propen-2-yl)-3-(3,4-d imethoxyphenyl)benzothiophene (process E; compound no. 105)

2-(4-Morpholinocarbonyl)-5-bromo-3-(3,4-dimethoxyphenyl)benzothiophene (2.0 g; 0.005 mole) prepared according to process A, 1,2-dimethoxyethane (50 ml), palladium tetrakis (triphenylphosphine) (0.2 g), propen-2-ylboronic acid (0.5 g; 0.006 mole) and 2M aqueous sodium carbonate (20 cc) are successively introduced into a flask under an inert atmosphere. The mixture is taken to reflux temperature for eight hours, then poured into a mixture of water and ice. The beige product obtained by precipitation is separated by filtration, rinsed with water and dried in the air. By chromatography on silica, compound no. 105 (1.5 g; yield=81.5%) is obtained, m.p. 135° C.

EXAMPLE 106

2-(4-Morpholinocarbonyl)-3-(4-methoxyphenyl) benzothiophene (process F; compound no. 106)

5-Amino-2-(4-morpholinocarbonyl)-3-(4-methoxyphenyl)benzothiophene (1.0 g; 0.0027 mole) and distilled tetrahydrofuran (THF; 50 ml) are introduced into a flask under an inert atmosphere. The mixture is taken to reflux temperature, then tert-butyl nitrite (0.7 ml; 0.0054 mole) dissolved in THF (20 ml) is poured in drop by drop. After three hours, the reaction mixture is treated with water, extracted with $CH_2Cl_2$, washed with water and dried over magnesium sulphate. After evaporation and chromatography, compound no. 106 (0.5 g; yield=53%) is isolated, m.p. 131° C.

EXAMPLE 107

2-(N,N-Diethylcarboxamide)-3-(3,4-dimethoxyphenyl)benzothiophene (process G; compound no. 107)

3-(3,4-Dimethoxyphenyl)benzothiophene-3-carboxylic acid (25 g; 0.08 mole) prepared according to process D, 1,2-dichloroethane (300 ml ), thionyl chloride (12 ml, 0.16 mole) and DMF (1 ml) are introduced into a flask. The mixture is progressively heated to reflux temperature; the solid dissolves little by little to provide a clear yellow solution. After four hours, the solvents are evaporated to provide 2-(chlorocarbonyl)-3-(3,4-dimethoxyphenyl)benzothiophene (24.7 g; yield=96%).

This product (2.5 g; 0.0075 mole) is immediately reacted with N,N-diethylamine (4 cc; 0.0375 mole) in THF (100 ml) to provide, after treatment with water and extraction with ethyl acetate, 2-(N,N-diethylcarboxamide)-3-(3,4-dimethoxyphenyl)benzothiophene (2.5 g; yield=90%) which crystallizes by trituration in pentane. m.p.=113° C. (compound no. 107).

EXAMPLE 108

3-(3,4-Dimethoxyphenyl)-2-ethoxycarbonylindenone (process G)

a) Thionyl chloride (25 g) is added to 2-(3,4-dimethoxybenzoyl)benzoic acid (15 g) and the mixture is heated to 50° C. until the evolution of gas has ended. At the end of the reaction, toluene is added and the mixture is evaporated to remove the excess $SOCl_2$. The acid chloride obtained is an orange solid.

b) The acid chloride is reacted with a slight excess of ethyl malonate magnesium enolate in toluene (prepared from ethyl malonate and magnesium ethylate). The reaction mixture is poured into dilute sulphuric acid and extracted with ethyl acetate. After washing with water and drying, the solvent is evaporated and a red oil is obtained which is used as such in the following stage.

c) The oil obtained above is heated to reflux temperature with a 5% solution of sodium carbonate (300 ml) for 35 minutes. A red solid forms. The mixture is cooled, the aqueous phase is removed by decantation and water (300 ml) is again added; the mixture is again heated to reflux temperature for 35 minutes. It is cooled, filtered, washed with water and dried. The indenone is obtained in the form of an orange solid (m.p. 130° C.; yield 49%; compound no. 108).

EXAMPLE NO. 109

3-(3,4-Dimethoxyphenyl)-2-morpholinocarbonylindenone

The indenone obtained in Example 108 (0.9 g) is heated with morpholine (10 ml) for 1 hour. The reaction mixture is poured into a solution of dilute hydrochloric acid and extracted with ethyl acetate, washed with water and concentrated. The product is obtained with a yield of 98% (m.p.=71.5°; compound no. 109).

EXAMPLE NO. 110

1-(3,4-Dimethoxyphenyl)-2-morpholinocarbonyl-3-hydroxyindene

The indenone from Example 109 (0.5 g) is reduced with $NaBH_4$ (0.05 g) and cerium chloride (0.5 g) in methanol (20 ml). The reaction in ended after 10 minutes and the reaction mixture is poured into water. The pH is taken to 5 by means of dilute HCl and the mixture is extracted with ethyl acetate. It is washed with water and the solvent is evaporated. Indenol (0.49 g; m.p. 134° C.) is obtained (yield: 99%; compound no. 110).

EXAMPLE NO. 111

2-Morpholinocarbonyl-3-(3,,4-dimethoxyphenyl)-6-mehoxyindene (process H)

a) Sodium (0.8 g) in reacted with absolute ethanol (100 ml) in a reactor. Then 3,4-dimethozybenzoylacetomorpholide (10 g) is then added and the mixture stirred for 15 minutes. 3-Methoxybenzyl chloride (5.3 g) in then added. The reaction mixture is taken to reflux temperature for 1 hour 30 minutes and concentrated under reduced pressure. It is taken up in water and dilute HCl and extracted with ethyl acetate. An orange oil is obtained.

b) To this oil (5.1 g) is added polyphosphoric acid (53 g), and the mixture is heated to 70° C. for 6 hours. Water is poured into the reaction mixture, which is stirred until it has dissolved, and then extracted with ethyl acetate. The product is purified by chromatography (eluent:ethyl acetate). Yield: 25%. m.p.=115° C. (compound no. 111).

EXAMPLE NO. 112

2-Morpholinocarbonyl-3-(3,4-dimethoxyphenyl)-5,6-methoxyindene (process I)

a) 3,4-(Dimethoxybenzoyl)acetomorpholide is condensed with veratraldehyde in acetic acid in the presence of piperidine and acetic anhydride. The mixture is heated to 100° C., poured into water, extracted with ethyl acetate, and the organic phase is washed with saturated $K_2CO_3$. The product is purified on silica, eluting with a 10:90 heptane/ethyl acetate mixture. A red solid of m.p. 150° C. is obtained.

b) The ethylenic ketone in then reduced with $NABH_4$ in the presence of cerium chloride in methanol. The allyl alcohol is thus obtained in a yield of 83% (m.p. 110° C.).

c) The allyl alcohol obtained above (2.2 g) is placed in toluene (80 ml) with a catalytic quantity of paratoluenesulphonic acid. The mixture is taken to reflux temperature for 5 hours, removing the water formed in the reaction. The reaction mixture is poured into water and decanted, washed with dilute potassium bicarbonate and then again with water. A light brown powder (1.9 g) is obtained (compound no. 112).

The following compounds were prepared using one of the preceding processes. Their structure and their physicochemical characteristics, and the process for obtaining them, are indicated in Table (I) below.

This table brings together, in addition, the structures and properties of the products of Examples 101 to 112. These compounds have formula (II) in which $R_{15}$ is H and $NR_{11}R_{12}$ is a 4-morpholino radical.

The structures are given in Table (I) below by means of the radicals $K_{110}$, $R_{13}$, $R_{14}$, $R_{16}$, $R_{17}$, $R_{18}$ and $R_{19}$ of formula (II).

TABLE I

| Compound N° | $K_{110}$ | $R_{13}$ | $R_{14}$ | $R_{16}$ | $R_{17}$ | $R_{18}$ | $R_{19}$ | m.p. | logP | Process |
|---|---|---|---|---|---|---|---|---|---|---|
| 101 | S | $OCH_3$ | $OCH_3$ | H | I | H | H | 214 | 4.4 | D |
| 113 | S | $OCH_3$ | $OCH_3$ | H | Cl | H | H | 166.5 | 3.9 | D |
| 114 | S | $OCH_3$ | $OCH_3$ | H | Br | H | H | 180 | 4.1 | D |
| 102 | S | $OCH_3$ | $OCH_3$ | H | 4-Cl—$C_6H_4$CONH | H | H | 247 | 4.8 | C |
| 115 | S | $OCH_3$ | $OCH_3$ | H | $CH_3$CONH | H | H | 140 | 2.4 | C |
| 116 | S | $OCH_3$ | $OCH_3$ | H | $CF_3$CONH | H | H | 198 | 3.5 | C |
| 103 | S | $OCH_3$ | $OCH_3$ | H | $NH_2$ | H | H | 213 | * | B |
| 104 | S | $OCH_3$ | $OCH_3$ | H | $NO_2$ | H | H | 144.5 | 3 | A |
| 117 | S | $OCH_3$ | $OCH_3$ | H | F | H | H | 146 | 3.4 | A |
| 118 | S | $OCH_3$ | $OCH_3$ | H | H | H | H | 123.5 | 3.3 | A |
| 119 | S | $OCH_3$ | $OCH_3$ | H | H | H | $NO_2$ | 269 | 3 | A |
| 120 | S | $OCH_3$ | $OCH_3$ | H | $C_6H_5$OCONH | H | H | 173 | 4.5 | C |
| 121 | S | $OCH_3$ | $OCH_3$ | H | H | H | $NH_2$ | 205 | * | B |
| 122 | S | $OCH_3$ | $OCH_3$ | H | H | H | F | 150 | 3.4 | A |
| 123 | S | $OCH_3$ | $OCH_3$ | H | H | H | Br | 205 | 4.1 | D |
| 124 | S | $OCH_3$ | $OCH_3$ | H | H | H | Cl | 186 | 3.9 | A |
| 125 | S | $OCH_3$ | $OCH_3$ | H | H | Cl | H | 192 | 3.9 | A |
| 126 | S | $OCH_3$ | $OCH_3$ | H | H | H | $C_6H_5$ | 191 | 5.0 | E |
| 127 | S | $OCH_3$ | $OCH_3$ | H | H | H | $CH_3$ | 167 | 3.8 | A |
| 128 | S | $OCH_3$ | $OCH_3$ | Cl | H | H | H | 151 | 3.9 | E |
| 129 | S | $OCH_3$ | $OCH_3$ | F | H | H | H | 167 | 3.4 | A |
| 130 | S | $OCH_3$ | $OCH_3$ | $CH_3$ | H | H | H | 150 | 3.8 | E |
| 131 | S | $OCH_3$ | $OCH_3$ | H | H | H | $NHCOCF_3$ | 226 | 3.5 | C |
| 132 | S | $OCH_3$ | $OCH_3$ | H | H | H | $NHCOCH_3$ | 210 | 2.4 | C |
| 133 | S | $OCH_3$ | $OCH_3$ | H | $CF_3$ | H | H | 164 | 4.1 | A |
| 105 | S | $OCH_3$ | $OCH_3$ | H | $H_2C=C(CH_3)$ | H | H | 135 | 4.3 | E |
| 134 | S | $OCH_3$ | $OCH_3$ | H | thienyl-3 | H | H | 188 | 4.7 | E |
| 135 | S | $OCH_3$ | $OCH_3$ | H | $C_6H_5$ | H | H | 208 | 5.0 | E |
| 136 | O | $OCH_3$ | $OCH_3$ | H | $NO_2$ | H | H | 152 | 2.5 | A |
| 137 | O | $OCH_3$ | $OCH_3$ | H | H | H | H | 153 | 2.7 | F |
| 138 | O | $OCH_3$ | $OCH_3$ | H | Cl | H | H | 135 | 3.4 | D |
| 139 | O | $OCH_3$ | $OCH_3$ | H | Br | H | H | 133 | 3.6 | D |
| 140 | O | $OCH_3$ | $OCH_3$ | H | $NH_2$ | H | H | 198 | * | B |
| 141 | $NCH_3$ | $OCH_3$ | $OCH_3$ | H | $NO_2$ | H | H | 190 | 2.7 | A |
| 142 | $NCH_3$ | $OCH_3$ | $OCH_3$ | H | $NH_2$ | H | H | 184 | * | B |
| 143 | S | H | $OCH_3$ | H | $NO_2$ | H | H | 106 | 3.5 | A |
| 144 | S | H | $OCH_3$ | H | $NH_2$ | H | H | 210 | * | B |
| 106 | S | H | $OCH_3$ | H | H | H | H | 131 | 3.7 | F |
| 145 | O | H | $OCH_3$ | H | $NO_2$ | H | H | 141 | 3 | A |
| 146 | O | H | $OCH_3$ | H | $NH_2$ | H | H | 196 | * | B |
| 147 | O | H | $OCH_3$ | H | H | H | H | | 3.2 | F |
| 111 | $CH_2$ | $OCH_3$ | $OCH_3$ | H | H | $OCH_3$ | H | 115 | 2.5 | H |
| 112 | $CH_2$ | $OCH_3$ | $OCH_3$ | H | $OCH_3$ | $OCH_3$ | H | 175 | 2.1 | I |
| 110 | CHOA | $OCH_3$ | $OCH_3$ | H | H | H | H | 134 | 2.0 | G |
| 148 | CHOAC | $OCH_3$ | $OCH_3$ | H | H | H | H | 110 | 2.7 | C |
| 149 | $CH_2$ | H | $OCH_3$ | H | $OCH_3$ | $OCH_3$ | H | 162.4 | 2.5 | I |

*Synthetic intermediates
Ac is $CH_3$—CO—

Table (II) brings together in addition the structures and physicochemical properties of compounds of formula (II) in which $K_{110}$ is a sulphur atom, $R_{13}$, and $R_{14}$ are methoxy radicals, and $R_{15}$, $R_{16}$, $R_{18}$ and $R_{19}$ are hydrogen atoms; $R_{17}$ and $NR_{11}R_{12}$ are indicated in Table (II). The compounds were prepared according to process G.

TABLE (II)

| Compound no. | $R_{17}$ | $NR_{11}R_{12}$ | m.p. | Log P |
|---|---|---|---|---|
| 150 | H | N-methylethylamino | 95 | 3.6 |
| 151 | H | bis(methoxyethyl)amino | 90 | 3.7 |
| 107 | H | N-diethylamino | 113 | 4.1 |
| 152 | H | 2,6-dimethylmorpholino | 150 | 4.2 |
| 153 | H | piperidino | 110 | 4.3 |
| 154 | H | pyrrolidino | 119 | 3.7 |
| 155 | H | N-dimethylamino | 129 | 3.1 |
| 156 | H | N-methylhydroxyethylamino | 84 | 2.8 |
| 157 | H | 2-hydroxymethylpiperidino | 60 | 3.8 |

TABLE (II)-continued

| Compound no. | $R_{17}$ | $NR_{11}R_{12}$ | m.p. | Log P |
|---|---|---|---|---|
| 158 | H | N-methylmethoxyethylamino | syrup | 3.4 |
| 159 | H | 2-methoxymethylpiperidino | 123 | 4.5 |
| 160 | H | 2-hydroxymethylpyrrolidino | 74 | 3.3 |
| 161 | H | 4-hydroxypiperidino | 166 | 2.2 |
| 162 | H | 4-oxopiperidino | 148 | 3.0 |
| 163 | H | 2-methoxymethylpyrrolidino | 60 | 3.9 |
| 164 | H | 3-hydroxypiperidino | 90 | 3.1 |
| 165 | H | 4-methoxypiperidino | 139 | 2.8 |
| 166 | H | 3-methoxypiperidino | 60 | 3.8 |
| 167 | F | N-methylethylamino | 103 | 3.8 |
| 168 | F | 2,6-dimethylmorpholino | 134 | 4.4 |
| 169 | F | N-methylmethoxyethylamino | syrup | 3.6 |
| 170 | F | bis(dimethoxyethyl)amino | 99 | 3.9 |

EXAMPLES 171 to 184

2-Chloro-3',4'-dimethoxy-5-nitrobenzophenone (intermediate product for the preparation of the products of formula (II) in which $K_{110}$ is O, S or $-N(R_{110})$)

2-Chloro-5-nitrobenzoyl chloride (11 g; 0.05 mole), 1,2-dimethoxybenzene (20 ml; 0.15 mole) and anhydrous ferric chloride (0.5 g) are successively introduced into a flask. The mixture is progressively heated to 150° C., and maintained at this temperature for 1 hour. After cooling, the reaction mixture is poured into 1N HCl (200 ml), then extracted with dichloromethane (3×200 ml). After washing with a sodium bicarbonate solution, the organic phase in dried over $MgSO_4$ and then concentrated under reduced pressure to provide a brown oil. By trituration with pentane (300 ml), 2-chloro-3',4'-dimethozy-5-nitrobenzophenone (12.5 g; yield: 78%) is isolated in the form of a beige solid of m.p. 138° C. (compound no. 171).

The compounds which follow were obtained in analogpus conditions: their structures and their physicochemical characteristics are indicated in the table below. These compounds are products of formula (XII') in which $R_{15}$ is H, $R_{14}$ is a methoxy radical and $A_1$, $R_{13}$, $R_{16}$, $R_{17}$, $R_{18}$ and $R_{19}$ have the meanings indicated in Table (III) which is shown below.

Examples 201 to 253 relate to products of sub-family (II) of formula (III).

EXAMPLE 201

2-(3,4-Dimethoxyphenyl)-4-(4-fluorophenyl)-1-morpholinocarbonylbenzene 2-(3,4-Dimethoxyphenyl)-4-(4-fluorophenyl)-benzoic acid (compound 204 1.6 g; 0.00454 mole), tetrahydrofuran (50 ml) and diimidazolecarbonyl (0.92 g; 0.0057 mole) are introduced into a 100 ml flask. The mixture is stirred at 20° C. for 2 hours. Morpholine (1 ml; 0.0113 mole) is then added and the mixture is maintained under stirring for six hours. The reaction mixture is poured into distilled water (150 ml) and the precipitate is filtered, washed with water (100 ml) and then dried in the air. 2-(3,4-Dimethoxyphenyl)-4-(4-fluorophenyl)-1-morpholinocarbonylbenzene (1.3 g; yield: 68.4%) in thus obtained in the form of a white solid of m.p. 153° C. (compound 201).

Compounds no. 201 to 231 were obtained in an identical manner. These compounds have as their formula formula (III) in which $R_{23}$ and $R_{24}$ are methoxy groups, $R_{25}$, $R_{28}$ and $R_{29}$ are the hydrogen atom and $R_{26}$, $R_{27}$, and $Z_2$ have the meanings given below in Tables (IV) and (IV') which are given further on.

Another sub-assembly of products have, as their formula, formula (III) in which $R_{23}$ and $R_{24}$ together constitute a divalent mothylenedioxy radical, $R_{25}$, $R_{26}$, $R_{28}$ and $R_{29}$ are the hydrogen atom, and $R_{27}$ and $Z_2$ have the meanings given below in Table (V).

TABLE III

| Compound N° | $R_{16}$ | $R_{13}$ | $A_1$ | $R_{17}$ | $R_{18}$ | $R_{19}$ | m.p. °C. |
|---|---|---|---|---|---|---|---|
| 171 | H | $CH_3O$ | Cl | $NO_2$ | H | H | 138 |
| 172 | H | $CH_3O$ | Cl | H | $NO_2$ | H | 140 |
| 173 | H | $CH_3O$ | F | H | H | H | 84 |
| 174 | H | $CH_3O$ | F | F | H | H | 125 |
| 175 | H | $CH_3O$ | Cl | H | H | $NO_2$ | 139.5 |

TABLE III-continued

| Compound N° | $R_{16}$ | $R_{13}$ | $A_1$ | $R_{17}$ | $R_{18}$ | $R_{19}$ | m.p. °C. |
|---|---|---|---|---|---|---|---|
| 176 | H | $CH_3O$ | F | H | H | F | 189 |
| 177 | H | $CH_3O$ | F | H | H | Cl | 167 |
| 178 | H | $CH_3O$ | F | H | Cl | H | 134 |
| 179 | H | $CH_3O$ | F | H | $NO_2$ | H | 140 |
| 180 | H | $CH_3O$ | F | H | H | $CH_3$ | 110 |
| 181 | F | $CH_3O$ | F | H | H | H | 102 |
| 182 | H | $CH_3O$ | F | $CF_3$ | H | H | 79 |
| 183 | H | H | Cl | H | $NO_2$ | H | 103 |
| 184 | F | $CH_3O$ | F | F | F | F | 77 |

TABLE (IV)

| No. | $Z_2$ | $R_{27}$ | m.p. | log P |
|---|---|---|---|---|
| 201 | morpholino | 4-fluorophenyl | 153 | 4.1 |
| 202 | morpholino | phenyl | 130 | 4.0 |
| 203 | morpholino | 4-methylphenyl | 129 | 4.6 |
| 204 | $N(CH_3)CH_2CH_2OCH_3$ | Br | syrup | 3.2 |
| 205 | $N(C_2H_5)_2$ | Br | 82 | 4.0 |
| 206 | $N(CH_3)C_2H_5$ | Br | 85 | 3.4 |
| 207 | pyrrolidino | Br | 96 | 3.5 |
| 208 | morpholino | Cl | 108 | 2.9 |
| 209 | $N(CH_3)C_2H_5$ | Cl | 68 | 3.3 |
| 210 | $N(CH_3)CH_2CH_2OCH_3$ | Cl | syrup | 3.1 |
| 211 | $N(C_2H_5)_2$ | Cl | 54 | 3.8 |
| 212 | $N(CH_3)CH_2H_5$ | 2-propenyl | 98 | 3.6 |
| 213 | $N(CH_3)CH_2CH_2OCH_3$ | 2-propenyl | 78 | 3.4 |
| 214 | $N(C_2H_5)_2$ | 2-propenyl | 68 | 4.1 |
| 215 | $N(CH_3)C_2H_5$ | p-tolyl | 130 | 5.0 |
| 216 | $N(CH_3)CH_2CH_2OH$ | p-tolyl | 130 | 4.2 |
| 217 | $N(CH_3)_2$ | p-tolyl | 109 | 4.5 |
| 218 | $N(CH_3)C_2H_5$ | $CH_3S$ | 110 | 3.2 |
| 219 | $N(C_2H_5)_2$ | $CH_3S$ | 73 | 3.7 |
| 220 | morpholino | $CH_3S$ | 132 | 2.8 |
| 221 | $N(CH_3)CH_2CH_2OCH_3$ | $CH_3S$ | 63 | 3.0 |
| 222 | morpholino | Br | 123 | 3.0 |

TABLE (IV')

| No. | $Z_2$ | $R_{16}$ | m.p. | log P |
|---|---|---|---|---|
| 223 | morpholino | Br | 55 | 3.0 |

TABLE (V)

| No. | $Z_2$ | $R_{27}$ | m.p. | log P |
|---|---|---|---|---|
| 224 | morpholino | Br | 145° C. | 2.9 |
| 225 | $N(CH_3)C_2H_5$ | Br | syrup | 3.4 |
| 226 | $N(CH_3)CH_2CH_2OCH_3$ | Br | syrup | 3.2 |
| 227 | $N(C_2H_5)_2$ | Br | syrup | 3.9 |
| 228 | $N(CH_3)C_2H_5$ | 4-fluorophenyl | 98° C. | 4.5 |
| 229 | morpholino | 4-fluorophenyl | 170° C. | 4.0 |
| 230 | $N(CH_3)C_2H_5$ | p-tolyl | 148° C. | 5.0 |
| 231 | morpholino | p-tolyl | 137° C. | 4.5 |

EXAMPLE 232

2-(3,4-dimethoxyphenyl)-4-(4-fluorophenyl)benzoic acid (compound 232)

Ethyl 2-(3,4-dimethoxyphenyl)-4-(4-fluorophenyl)benzoate (2.8 g; 0.074 mole), absolute ethanol (50 ml) and 10N sodium hydroxide (2 ml) are introduced into a 100 ml flask. The mixture is taken to reflux temperature for two hours, then poured over 1N hydrochloric acid (150 ml). The precipitate is filtered on fritted glass, washed with water,

EXAMPLE 233

Ethyl 2-(3,4-dimethoxyphenyl)-4-(4-fluorophenyl)benzoate (compound 233)

1,2-Dimethoxyethane (30 ml) which has been degassed with argon is introduced into a 250 ml three-necked flask, then ethyl 4-bromo-2-(3,4-dimethoxyphenyl) benzoate (3.65 g; 0.010 mole; compound 209), palladium tetrakis(triphenyl)phosphine (0.1 g), 4-fluorophenylboronic acid (1.7 g; 0.012 mole) and 2M sodium carbonate (20 ml) are added. After refluxing for 8 hours, the reaction mixture is poured into distilled water (100 ml). The mixture is then extracted with dichloromethane (2×100 ml), washed with water (100 ml), dried over magnesium sulphate, passed over a layer of silica and then evaporated. Ethyl 2-(3,4-dimethoxyphenyl)-4-(4-fluorophenyl)benzoate (3.4 g; yield: 89.5%) is thus obtained, m.p. 127° C. (compound 233).

The compounds of formula (III) in which $R_{23}$ and $R_{24}$ are methoxy groups, and $R_{25}$, $R_{26}$, $R_{28}$ and $R_{29}$ are the hydrogen atom, $R_{27}$ and $Z_2$ having the meanings indicated in Table (VI) below, were obtained in an identical manner.

TABLE (VI)

| Compound No. | $Z_2$ | $R_{27}$ | m.p. | log P |
|---|---|---|---|---|
| 233 | $OC_2H_5$ | 4-F-phenyl | 127 | * |
| 234 | morpholino | 3,4-dimethoxyphenyl | 189 | 3.4 |
| 235 | morpholino | $(CH_3)_2 C=CH-$ | 97 | 3.8 |
| 236 | morpholino | $H_2C=C(CH_3)-$ | 128 | 3.2 |
| 237 | morpholino | 4-chlorophenyl | 144 | 4.7 |
| 238 | morpholino | 3-thienyl | 151.5 | 3.6 |
| 239 | morpholino | 4-piperonyl | 138 | 3.4 |
| 249 | $OC_2H_5$ | 4-methoxyphenyl | 125 | * |
| 241 | OH | p-tolyl | 215 | * |
| 242 | $OC_2H_5$ | p-tolyl | 84 | * |
| 243 | OH | 4-methoxyphenyl | 202 | * |

*synthetic intermediate

The compounds of formula (III) in which $R_{23}$ and $R_{24}$ together constitute a divalent methylenedioxy radical, $R_{25}$, $R_{26}$, $R_{28}$ and $R_{29}$ are the hydrogen atom, and $R_{27}$ and $Z_2$ have the meanings given below in Table (VII) were also obtained.

TABLE (VII)

| No. | $Z_2$ | $R_{27}$ | m.p. |
|---|---|---|---|
| 244 | OH | Br | 194 |
| 245 | $OH_2H_5$ | 4-fluorophenyl | 72 |
| 246 | $OC_2H_5$ | p-tolyl | 98 |
| 247 | OH | 4-fluorophenyl | 177 |
| 248 | OH | p-tolyl | 180 |
| 249 | OH | phenyl | 177 |

EXAMPLE 250

Ethyl 4-bromo-2-(3,4-dimethoxyphenyl)benzoate (compound no. 250)

Ethyl 4-amino-2-(3,4-dimethoxyphenyl)benzoate (20.0 g; 0.066 mole; compound 252) and acetic acid (200 ml) are introduced into a 1000 ml three-necked flask. After dissolution, 47% strength hydrobromic acid (60 ml) is added, the mixture is cooled to 0° C. and then distilled water (150 ml) is added. Sodium nitrite (4.6 g; 0.066 mole) dissolved in water (30 ml) is poured in. Stirring is continued at between 0° and 5° C. for one hour, then the mixture is poured onto a solution of cuprous bromide (9.5 g; 0.066 mole) in 47% strength hydrobromic acid (100 ml). The reaction mixture is heated to 65% for one hour, then poured into water. The precipitate formed is filtered, rinsed with water and then dried in the air. Ethyl 4-bromo-2-(3,4-dimethoxyphenyl)benzoate (18.4 g; yield: 76.3%) is thus obtained, m.p. 53° C. (compound 250).

The compounds of formula (III) in which $R_{23}$ and $R_{24}$ are methoxy groups, $R_{25}$, $R_{26}$, $R_{28}$ and $R_{29}$ are the hydrogen atom, $Z_2$ has the meaning given below and $R_{27}$ is the bromine atom were obtained in an identical manner.

| Compound No. | $Z_2$ | $R_{27}$ | m.p. |
|---|---|---|---|
| 250 | $OC_2H_5$ | Br | 53 |
| 251 | OH | Br | 181.5 |

EXAMPLE 252

Ethyl 4-amino-2-(3,4-dimethoxyphenyl)benzoate (compound 252)

1,2-Dimethoxy-1,2-ethane (200 ml) and then ethyl 4-amino-2-bromobenzoate (compound 218; 17 g; 0.07 mole), tetrakis(triphenyl)phosphine (0.3 g) and 2M sodium carbonate (100 ml) are introduced into a 500 ml flask. After boiling under reflux for 8 hours, the reaction mixture is poured into water (600 ml). The solid obtained is filtered off, rinsed with water and dried in the air. It is then rinsed with pentane (50 ml). Ethyl 4-amino-2-(3,4-dimethoxyphenyl)benzoate (20.0 g; yield: 95%) is thus obtained, m.p. 127° C. (compound 252).

The products of formula (III) in which $R_{23}$ and $R_{24}$ are methoxy groups, $R_{25}$, $R_{28}$ and $R_{29}$ are the hydrogen atom, and $Z_2$, $R_{27}$ and $R_{26}$ have the meanings given below were obtained in an identical manner.

| Compound No. | $Z_2$ | $R_{27}$ | $R_{26}$ | m.p. |
|---|---|---|---|---|
| 252 | $OC_2H_5$ | $NH_2$ | H | 127 |
| 253 | OH | H | $NO_2$ | 182 |

EXAMPLE 254

Ethyl 4-amino-2-bromobenzoate (compound 254)

Ethyl 2-bromo-4-nitrobenzoate (46 g; 0.17 mole), ethanol (250 ml), iron powder (28 g; 0.5 mole) and concentrated hydrochloric acid (20 ml) are successively introduced into a 1 liter flask. The mixture is taken to reflux temperature for four hours. After cooling, the reaction mixture is treated with a saturated solution of sodium bicarbonate (500 ml) and extracted with ethyl acetate (5×300 ml). After drying over magnesium sulphate, filtration and evaporation, ethyl 4-amino-2-bromobenzoate (35.2 g; yield: 86%) is isolated, m.p. 93° C. (compound no. 254).

Examples 301 to 399 and 3100 to 3119 illustrate the preparation of compounds of formula (IV).

EXAMPLE NO. 301

N-[2-(3,4-dimathoxyphenyl)-6-phenylnicotinoyl]morpholine (compound no. 301) process (b)

Morpholine (1.8 g; 0.002 mole) is poured drop by drop into a solution of 2-(3,4-dimethoxyphenyl-6-phenyl)nicotinoyl chloride (1.9 g; 0.005 mole; compound no. 2) in tetrahydrofuran (60 ml), at 25°–30° C. The The hydrochloride precipitates as soon as pouring starts. After the end of the addition the mixture is left to react for 10 min, and the medium diluted with ethyl acetate (200 ml). The medium in washed with water (2×100 ml). The solution is dried over anhydrous magnesium sulphate, then concentrated under reduced pressure. An oil is obtained which crystallizes from ether. After filtration and drying, a beige powder (1.9 g; yield: 95%) is obtained, m.p. 185.5° C.

EXAMPLES NO. 304 TO 308

2-(3,4-dimethoxyphenyl)-6-phenylnicotinoyl chloride (compound no. 302)

A mixture of 2-(3,4-dimethoxyphenyl)-6-phenylnicotinic acid (compound no. 303; 1.8 g; 0.0054 mole) and thionyl chloride (20 ml) is heated to boiling point under reflux for 1 h. The medium is concentrated under reduced pressure. A yellow syrup (1.9 g; yield=100%) is obtained.

Working in the same manner, the nicotinoyl chlorides of formula (IV''') in which $Z_3$ is the chlorine atom and $R_{371}$ has the meanings given below, are obtained.

| Compound No. | $R_{371}$ | m.p. |
|---|---|---|
| 304 | H | syrup |
| 305 | Cl | 114 |
| 306 | F | 114 |
| 307 | Br | 106 |
| 308 | NC | 160 |

EXAMPLES NO. 303 AND 310 TO 313

2-(3,4-Dimethoxyphenyl)-6-phenylnicotinic acid (compound no. 303)

30% strength sodium hydroxide (2 ml) is added to a solution of ethyl 2-(3,4-dimethoxyphenyl)-6-phenylnicotinate (compound no. 309; 3.6 g; 0.01 mole) in 95% strength alcohol (100 ml). The reaction medium is heated for 2 h to 60°–70° C. The medium is concentrated under reduced pressure and the residue is dissolved in water (100 ml). The medium is acidified with concentrated hydrochloric acid (2 ml): a gum is released. The mixture is extracted with ethyl acetate (100 ml). The solution is washed with water (2×100 ml), dried over anhydrous magnesium sulphate and then concentrated under reduced pressure. A foam is obtained which is crystallized by trituration in ether (50 ml). After filtration and drying, a beige powder (2.5 g; yield=75%) is obtained, m.p. 178° C. Working in the same manner, the compounds of formula (IV''') in which $Z_3$ is the hydroxyl group and $R_{371}$ has the meanings indicated below, is obtained.

| Compound no. | $R_{371}$ | m.p. | Log P |
|---|---|---|---|
| 303 | H | 178 | |
| 310 | Cl | 145 | |
| 311 | F | 170 | |
| 312 | Br | 162 | |
| 313 | CN | 163 | |

EXAMPLES 309 AND 315 TO 317

Ethyl 2-(3,4-dimethoxyphenyl)-6-phenylnicotinate (compound no. 309): process a'

A mixture of ethyl 2-(3,4-dimethoxybenzoyl)-5-oxo-5-phenylvalerate (compound no. 314; 7.7 g; 0.02 mole), ammonium acetate (3.1 g; 0.04 mole) and acetic acid (30 ml) is heated to reflux temperature for 4 hours. The reaction medium is poured into water (300 ml): an oil in released. The latter is extracted with ethyl acetate (200 ml). The organic solution is washed with water (3×100 ml), then dried over anhydrous magnesium sulphate and concentrated under reduced pressure. A light brown oil (4.5 g; yield: 62%) is obtained which corresponds to ethyl 2-(3,4-dimethoxyphenyl)-6-phenylnicotinate.

Working in the same manner, the compounds of formula (IV''') in which $Z_3$ is ethoxy and $R_{371}$ has the following meanings, are obtained:

| Compound no. | $R_{371}$ | Physical characteristics |
|---|---|---|
| 315 | phenyl | syrup |
| 316 | 4-chlorophenyl | syrup |
| 317 | 4-fluorophenyl | syrup: refractive index = 1.611 |

EXAMPLES 318 TO 320

Working according to process a, as in the preceding example, and using the corresponding suitably substituted intermediates, the compounds below of formula (IV''') with $Z_3$=ethoxy were obtained.

| Compound no. | $R_{371}$ | Physical characteristics |
|---|---|---|
| 318 | 4-bromophenyl | syrup |
| 319 | 4-cyanophenyl | m.p. = 118° C. |
| 320 | 3-thienyl | syrup |

EXAMPLES 321 TO 344

Ethyl 2-(3,4-dimethoxybenzoyl)-5-oxo-5-phenylvalerate (compound no. 314)

3-Chloropropiophenone (8.4 g; 0.05 mole) is added to an alcoholic solution of the sodium salt of ethyl (3,4-dimethoxybenzoyl)acetate (13.7 g; 0.05 mole): the reaction is exothermic, and the temperature of the medium rises progressively from 24° C. to 35° C. It is left to react under stirring for ¾ hour (return to ambient temperature). The reaction medium is poured into water (400 ml); the product is released in the form of a gum. The latter is extracted with chloroform (300 ml).

The chloroform solution is washed with water (5×200 ml), then dried over anhydrous magnesium sulphate and concentrated under reduced pressure. A brown syrup (19.5 g) is obtained. The product crystallizes after dissolution in ether (100 ml). After filtration of the precipitate and drying the filter cake, a beige powder (15 g; yield: 77%) is obtained of m.p. 70° C., which corresponds to ethyl 2-(3,4-dimethoxybenzoyl)-5-oxo-5-phenylvalerate.

Working in the same manner, the compounds which are assembled in the following tables are obtained, which are of formula:

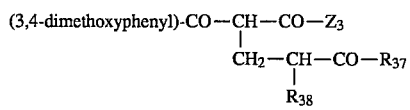

| Compound no. | $R_{37}$ | $R_{38}$ | $Z_3$ | m.p. |
|---|---|---|---|---|
| 321 | $C_6H_5$ | H | $OC_2H_5$ | 70 |
| 322 | 4-Cl $C_6H_4$ | H | $OC_2H_5$ | 109 |
| 323 | 4-F $C_6H_4$ | H | $OC_2H_5$ | 100 |
| 324 | 4-Br $C_6H_4$ | H | $OC_2H_5$ | 98 |
| 325 | t-$C_4H_9$—$C_6H_4$ | H | morpholino | 134 |
| 326 | 4-Cl $C_6H_4$ | $CH_3$ | morpholino | 98 |
| 327 | 4-F $C_6H_4$ | $CH_3$ | morpholino | 88 |
| 328 | t-$C_4H_9$— | H | morpholino | 145 |
| 329 | $(CH_3)_2$=CH— | H | morpholino | 114 |
| 330 | 4-Br $C_6H_4$ | H | $C_2H_5O$ | 98 |
| 331 | 4-Cl $C_6H_4$ | H | morpholino | 145 |
| 332 | 4-$C_6H_5$—$C_6H_4$ | H | morpholino | 178 |
| 333 | 4-$CH_3$ $C_6H_4$ | H | morpholino | 148 |
| 334 | 4-Br $C_6H_4$ | H | morpholino | 164 |
| 335 |  | H | morpholino | 90 |
| 336 | 2-Cl $C_6H_4$ | H | morpholino | 100 |
| 337 | 4-iso-$C_3H_7$—$C_6H_4$ | H | morpholino | 100 |
| 338 | 4-$CH_3O$ $C_6H_4$ | H | morpholino | 130 |
| 339 | 2-thienyl | H | morpholino | 146 |
| 340 | 3-thienyl | H | morpholino | 148 |
| 341 | 1-naphthyl | H | morpholino | 160 |
| 342 | 2-naphthyl | H | morpholino | 150 |
| 343 | 3-furyl | H | morpholino | 150 |
| 344 | 2-$CH_3$—$C_6H_4$ | H | morpholino | 132 |

EXAMPLE 345

Preparation of N-[5-(4-chlorophenyl)-2-(3,4-dimethoxybenzoyl)-5-nicotinoyl]morpholine (compound 345) (process a)

N-[5-(4-chlorophenyl)-2-(3,4-dimethoxybenzoyl-5-oxovaleryl]morpholine (compound 346) (46 g; 0.1 mole) and ammonium acetate (15.4 g; 0.2 mole) are dissolved in acetic acid (150 ml). The mixture is heated to boiling point under reflux for 4 hours, while bubbling a current of air into the medium. The medium is cooled to ambient temperature and poured into water (0.5 l): a gum is released. The latter is extracted with methylene chloride (200 ml). The methylene chloride solution is washed with water, then treated with activated charcoal. The solution is concentrated. A brown syrup is obtained which is crystallised by trituration in ether (200 ml). The crystallised product is filtered, the filter cake is washed with ether and then dried under reduced pressure. A beige powder (21.2 g) is thus obtained of m.p. 152° C. (yield: 48%).

EXAMPLES 345 TO 394

Working according to one of the operating methods described in Examples 345 (process a) and 301 (process b), starting with suitably substituted intermediates, the derivative of formula (IV"") is obtained, the substituents, the process used and the physical characteristics of which are shown in the table which follows.

The substituted morpholino radicals are numbered from the oxygen atom, the free valency being carried by the nitrogen atom. The asterisk means that the compound is a synthetic intermediate.

| Compound no. | Xn | $R_{38}$ | $NR_{31}R_{32}$ | process | m.p. | Log P |
|---|---|---|---|---|---|---|
| 301 | — | H | morpholino | a | 185.5 | 3.3 |
| 345 | 4-Cl | H | morpholino | b | 148 | 4.0 |
| 347 | 4-Cl | H | $NCH_3(C_2H_5)$ | b | 156 | 4.4 |
| 348 | 4-Cl | H | $(CH_3OCH_2CH_2)_2N$ | b | syrup | 4.6 |
| 349 | 4-F | H | morpholino | b | 180 | 3.5 |
| 350 | 4-F | H | $NCH_3(C_2H_5)$ | b | 117 | 4.4 |
| 351 | 4-F | H | $(CH_3OCH_2CH_2)_2N$ | b | refractive index 1.587 | 4.0 |
| 352 | 4-F | H | $CH_3OCH_2CH_2NH$ | b | 138 | * |
| 353 | 4-F | H | $CH_3OCH_2CH_2N$—$CH_3$ | b | syrup | 3.7 |
| 354 | — | H | $CH_3OCH_2CH_2N$—$CH_3$ | b | syrup | 3.5 |

| | | | | -continued | | | |
|---|---|---|---|---|---|---|---|
| 355 | 4-CH—CH with Cl, Cl (structure) | H | morpholino | | a | 159 | 4.7 |
| 356 | 4-iC$_3$H$_7$ | H | morpholino | | a | 179 | 4.9 |
| 357 | 4-Cl | H | 2-methoxy-pyrrolidino | | b | 60 | 4.5 |
| 358 | 4-Cl | H | CH$_3$ \| NCH$_3$(nC$_3$H$_7$) | | b | syrup | 5.0 |
| 359 | — | H | CH$_3$ \| N—CH$_2$—CH=CH$_2$ | | | glass | 3.7 |
| 360 | — | H | NCH$_3$(i-C$_3$H$_7$) | | | | 4.0 |
| 361 | — | H | NCH$_3$(nC$_4$H$_9$) | | b | glass | 4.7 |
| 362 | 4-Cl | H | NCH$_3$(n-C$_4$H$_9$) | | b | syrup | 5.5 |
| 363 | 4-Cl | H | NCH$_3$(CH$_2$—CN) | | b | syrup | 3.6 |
| 364 | 4-Cl | H | (C$_2$H$_3$)$_2$N— | | b | syrup | 5.0 |
| 365 | — | H | NCH$_3$(n-C$_3$H$_7$) | | b | syrup | 4.2 |
| 367 | 4-Cl | CH$_3$ | morpholino | | a | 186 | 4.70 |
| 368 | 4-F | CH$_3$ | morpholino | | a | 180 | 4.1 |
| 369 | H | H | NCH$_3$(C$_2$H$_5$) | | b | 102 | 3.7 |
| 370 | H | H | (CH$_3$)$_2$N | | b | 70 | 3.2 |
| 371 | H | H | CH$_3$O(CH$_2$)$_2$—NH | | b | 101 | * |
| 372 | H | H | tetrahydro-furfurylamino | | b | 143 | * |
| 373 | 4-Cl | H | pyrrolidino | | b | 150 | 4.6 |
| 374 | 4-Cl | H | 2,6-dimethyl-morpholino | | b | 100 | 5.0 |
| 375 | 4-Cl | H | tetrahydro-furfurylamino | | b | 128 | * |
| 376 | 4-Cl | H | piperidino | | b | 144 | 5.1 |
| 377 | 4-Cl | H | 4-hydroxy-piperidino | | b | 150 | 3.0 |
| 378 | 4-Cl | H | CH$_3$ furfuryl-N | | b | syrup | 4.9 |
| 379 | 4-Cl | H | CH$_3$ \| CH$_3$O(CH$_2$)$_2$—N | | b | syrup | 4.2 |
| 381 | 4-Cl | H | tetrahydro-furfuryl-methylamino | | b | 100 | 4.6 |
| 384 | 4-CH$_3$ | H | morpholino | | a | 178 | 4.0 |
| 385 | 4-Br | H | morpholino | | a | 152 | 4.2 |
| 386 | 4-Cl | H | CH$_3$—N \| CH$_2$=CHCH$_2$ | | b | syrup | 4.44 |
| 387 | — | H | NC—CH$_2$CH$_2$—N \| CH$_3$ | | b | syrup | 3.9 |
| 388 | — | H | (C$_2$H$_5$)$_2$N | | b | syrup | 4.3 |
| 389 | 4-CH$_3$O | H | morpholino | | b | 210 | 3.3 |
| 390 | 4-Br | H | NCH$_3$(C$_2$H$_5$) | | a | syrup | 4.6 |
| 391 | 2-CH$_3$ | H | morpholino | | a | 158 | 4.0 |
| 392 | 2-Cl | H | morpholino | | a | 186 | 4.0 |
| 393 | 4-Br | H | CH$_3$ \| CH$_3$O—CH$_2$CH$_2$—N— | | b | syrup | 4.40 |
| 394 | 4-Cl | H | NCH$_3$(CH$_3$O) | | b | glass | 4.6 |

| Compound no. | Xn | R$_{38}$ | NR$_1$R$_2$ | process | m.p. | Log P |
|---|---|---|---|---|---|---|
| 366 | 4-Br | H | CH$_3$C—OCH$_2$CH$_2$—N \|\| \| O H$_3$C | b | syrup | 5.0 |

-continued

| No. | Xn | R₃₈ | NR₁R₂ | process | m.p. | Log P |
|---|---|---|---|---|---|---|
| 380 | 4-Br | H | HO—CH₂CH₂—N(CH₃)— | b | 178 | 3.8 |
| 382 | 4-CN | H | morpholino | b | 197 | 2.8 |
| 383 | 4-Cl | H | HO—CH₂CH₂—N(CH₃)— | b | 160 | 3.6 |
| 395 | | H | HOCH₂CH₂—N(CH₃)— | b | 164 | 2.9 |
| 396 | | H | CH₃C(=O)—OCH₂CH₂—N(H₃C)— | b | syrup | 4.3 |
| 397 | 4-Cl | H | CH₃C(=O)—OCH₂CH₂—N(CH₃)— | b | syrup | 5.0 |
| 398 | | H | (CH₃)₂N—CH₂—CH₂—N(CH₃)— | b | 229 | 3.70 |
| 399 | 4-CN | H | C₂H₅—N(CH₃)— | b | 139 | 3.2 |
| 3100 | 4-CN | H | CH₃O—CH₂CH₂—N(CH₃)— | b | syrup | 3 |

Products for which the biological results will not be given.

| Compound no. | Xn | R₃₈ | NR₁R₂ | process | m.p. | Log P |
|---|---|---|---|---|---|---|
| 3101 | 4-CH₃O | H | CH₃OCH₂CH₂—N(CH₃)— | b | syrup | 3.5 |
| 3102 | 4-CH₃O | H | HO—CH₃—CH₂—N(CH₃)— | b | syrup | 2.9 |
| 3103 | 4-CH₃O | H | CH₃C(=O)—OCH₂CH₂—N(CH₃)— | b | syrup | 4.3 |
| 3104 | 3-Cl | H | morpholino | b | 100 | 4.0 |
| 3105 | 3-Cl | H | C₂H₅—N(CH₃)— | b | syrup | 4.4 |
| 3106 | 3-Cl | H | (C₂H₅)₂N— | b | syrup | 5.0 |
| 3107 | 4-CF₃ | H | morpholino | a | 144 | 4.20 |
| 3108 | 4-CH₃O | H | (C₂H₅)₂N— | b | syrup | 4.3 |
| 3109 | 4-CH₃O | H | C₂H₅—N(CH₃)— | b | syrup | 3.7 |

EXAMPLES 3110 TO 3119

Working according to the operating method of Example 345 (precess a) from suitably substituted intermediates, the derivatives of formula (IV') in which $NR_{31}R_{32}$ is a morpholino radical and $R_{37}$ has the meanings which are indicated in the table which follows together with the physical characteristics of the products, are obtained.

| Compound no. | $R_{37}$ | Process | m.p. | Log P |
|---|---|---|---|---|
| 3110 | t-Butyl | a | 163 | 3.2 |
| 3111 | $(CH_3)_2C=CH-$ | a | 163 | 2.9 |
| 3112 | 3-thienyl | a | 194 | 3.0 |
| 3113 | 2-thienyl | a | 190 | 3.20 |
| 3114 | 1-naphthyl | a | 148 | 4.5 |
| 3115 | 2-naphthyl | a | 112 | 4.5 |
| 3116 | 2-furyl | a | 174 | 2.70 |

| Compound no. | $R_{37}$ | $Z_3$ [formula (XIV)] | Process | m.p. | Log P |
|---|---|---|---|---|---|
| 3117 | 3-thienyl | $CH_3O-(CH_2)_2-N(CH_3)-$ | b | syrup | 3.20 |
| 3118 | 3-thienyl | $CH_3(C_2H_5)N-$ | b | syrup | 3.40 |
| 3119 | 3-thienyl | $(C_2H_5)_2N$ | b | syrup | 3.9 |

Examples 401 to 458 illustrate the preparation of derivatives of compounds of formula (V).

EXAMPLE 401

Ethyl 3-(3,4-dimethoxyphenyl)-3-oxo-2-(dimethylaminoethylene)propionate (compound no. 401)

Ethyl 3,4-dimethoxybenzoyl acetate (20 g), toluene (80 ml) and dimethylformamide-dimethylacetal (20 g) are placed in a reactor. The mixture is heated to reflux temperature for two hours and then left at ambient temperature for one night. The solvent and the excess reagents are evaporated. The product is purified by passing over silica (eluent:ethyl acetate). A yellow syrup is obtained in a yield of 94%.

EXAMPLE 402

1-(3,4-Dimethoxyphenyl)-3-dimethylamino-2-morpholinocarbonylpropenone (compound no. 402)

3,4-Dimethoxybenzoylacetomorpholide (20 g), dimethylformamide-dimethylacetal (28 g) and dimethylformamide (20 ml) are loaded into a reactor. The mixture is heated to 60° C. for 7 hours, and left for one night at ambient temperature. The mixture is poured into water and the precipitate obtained is filtered off.

In this manner a yellow solid is obtained of m.p. 156.8° C., in a yield of 84%.

EXAMPLE 403

Working as in Examples 401 and 402, but using suitably substituted intermediates, the derivatives of formula (XV') in which $Ar_4$ has the preceding meaning, and in which $R_{43}$ and $R_{44}$ are methoxy groups, and $R_{45}$ and $R_{49}$ are the hydrogen atom, were obtained.

$X_4$ and $Z_4$ have the meaning indicated below:

| Compound no. | $X_4$ | $Z_4$ | characteristics |
|---|---|---|---|
| 403 | $N(CH_3)_2$ | $N(CH_3)(C_2H_5)$ | syrup |
| 404 | $N(CH_3)_2$ | $N(C_2H_5)_2$ | syrup |

EXAMPLE 405

5-Carbethoxy-2-(4-chlorophenyl)-4-(3,4-dimethoxyphenyl)pyrimidine (compound no. 405)

Absolute ethanol (20 ml) and sodium (0–3 g) are placed in a reactor. After dissolution, 4-chlorobenzamidine hydroiodide (3.7 g) is added. The mixture is heated to reflux temperature for one hour, and the enaminone synthesized in Example 401 (4.06 g) is added. The mixture is heated to reflux temperature for 2.5 hours, the solvent is evaporated, and the precipitate obtained is washed with water and dried. A white solid (4.2 g) is obtained, m.p. 115.4° C.

EXAMPLE 406

5-Carboxy-2-(4-chlorophenyl)-2-(3,4-dimethoxyphenyl)pyrimide (compound no. 406)

The product obtained in Example 404 (3.3 g) is dissolved in ethanol (100 ml) and treated with 10N sodium hydroxide (2 ml). The mixture is heated to 80° C. for one hour and evaporated. The residue is taken up in water and acidified with HCl. A yellow precipitate is obtained, which is filtered off and washed with water.

Yield 95%—m.p.: 258.1° C.

EXAMPLE 407

2-(4-Chlorophenyl)-4-(3,4-dimethoxyphenyl)-5-morpholinocarbonylpyrimidine (compound no. 407)

The acid obtained in Example 406 (1.5 g) is heated to 75° C. with thionyl chloride (35 ml) for 1.5 hours. The mixture is concentrated, dichloromethane is added and the mixture is again evaporated to remove the excess reagent completely. In this manner an orange solid is obtained.

This acid chloride is dissolved in ethyl ether (100 ml) and cooled to 0° C. A solution of morpholine (0.9 g) and pyridine (0.4 g) in ether (40 ml) is added drop by drop. After the addition, the mixture is stirred for 1.5 hours at ambient temperature. It is poured into water and extracted with ether, dried over magnesium sulphate and concentrated. After recrystallization from ether, a solid (1 g) is obtained of m.p. 168° C. (yield 48%).

EXAMPLE 408

2-(3,4-Dichlorophenyl)-4-(3,4-dimethoxyphenyl)-5-morpholinocarbonylpyrimidine (compound no. 408)

Absolute ethanol (10 ml) and sodium (0.1 g) are placed in a reactor. The mixture is stirred until dissolution, and 3,4-dichlorobenzamidine benzene sulphonate (1–35 g) is added. The mixture is heated to 60° C. for 30 minutes, and the enaminone prepared in Example 402 and absolute ethanol (15 ml) are added. The mixture is heated to reflux temperature for 5 hours, and the precipitate is filtered off and washed with cold ethanol and with heptane. It is dried. A solid is obtained of m.p. 181° C. (83% yield).

Working as in Examples 405 to 408 respectively, but starting from suitably substituted intermediates, the derivatives of formula (V) in which $R_{43}$ and $R_{44}$ are methoxy groups and $R_{45}$ and $R_{49}$ are hydrogen atoms, $Z_4$ and $R_{47}$ having the meanings indicated below, were obtained.

| Compound No. | Process as in Example No | $R_{47}$ | $Z_4$ | Characteristics | Log P |
|---|---|---|---|---|---|
| 409 | 405 | 3-nitro phenyl | $OC_2H_5$ | m.p. = 141° C. | * |
| 410 | 406 | " | OH | m.p. = 226° C. | * |
| 412 | 405 | phenyl | $OC_2H_5$ | m.p. = 98° C. | |
| 413 | 406 | " | OH | m.p. = 215° C. | |
| 414 | 407 | " | morpholino | m.p. = 172° C. | 2.3 |
| 415 | 407 | " | $N(CH_3)(C_2H_5)$ | m.p. = 100° C. | 2.7 |
| 416 | 407 | " | $N(CH_3)(CH_3OC_2H_4)$ | oil orange | 2.5 |
| 405 | 405 | 4-chlorophenyl | $OC_2H_5$ | m.p. = 115° C. | * |
| 407 | 407 | " | morpholino | m.p. = 168° C. | 3.0 |
| 417 | 405 | 3,4-dichlorophenyl | $OC_2H_5$ | m.p. = 74° C. | * |
| 418 | 406 | " | OH | m.p. = 267° C. | * |
| 408 | 408 | " | morpho- | m.p. = 181° C. | 3.7 |
| 420 | 407 | " | $N(C_2H_5)_2$ | m.p. = 122° C. | 3.6 |
| 421 | 407 | " | $N(CH_3)(C_2H_5)$ | m.p. = 146° C. | 4.1 |
| 422 | 405 or 423 | methylthio | $OC_2H_5$ | m.p. = 81° C. | * |
| 423 | 407 | " | morpholino | m.p. = 151° C. | * |
| 424 | 405 | 3-$CF_3$-phenyl | $OC_2H_5$ | oil | * |
| 425 | 408 | " | morpholino | m.p. = 149° C. | 3.2 |
| 426 | 406 | 3-$CF_3$-phenyl | OH | m.p. = 162° C. | |
| 427 | 408 | 4-bromophenyl | morpholino | m.p. = 169° C. | 3.2 |
| 428 | 407 | 3-$CF_3$-phenyl | $N(CH_3)(C_2H_5)$ | syrup | 3.6 |
| 429 | 407 | " | $N(C_2H_5)_2$ | m.p. = 98° C. | 4.1 |
| 430 | 408 | 4-bromophenyl | $N(C_2H_5)_2$ | syrup | 4.1 |
| 431 | 408 | 4-chlorobenzyl | morpholino | m.p. = 116° C. | 3.2 |

EXAMPLE 423

4-(3,4-dimethoxyphenyl)-2-methylthio-5-morpholinocarbonylpyrimidine (compound no. 423)

KOH (6.6 g) is dissolved in water (60 ml) in a reactor, then S-methylisothiourea sulphate (16.3 g) is added, and immediately afterwards the enaminone synthesized in Example 402 (13.6 g).

A precipitate forms after refluxing for 1.5 hours. It is filtered off, and the solid obtained is washed with water and dried; yield 58%, m.p.=151° C.

EXAMPLE 432

4-(3,4-dimethoxyphenyl)-2-methylsulfonyl-5-morpholinocarbonylpyrimidine (compound no. 432)

The pyrimidine obtained in Example 423 (9.5 g) is dissolved in dichloromethane (10 ml), and at a temperature of 0° C. metachloroperoxybenzoic acid (11 g) is added in portions. The mixture is stirred for 2.5 hours at ambient temperature. The excess per-acid is destroyed with sodium bisulphite, and the solution is then washed with bicarbonate. It is washed, and dried over magnesium sulphate. After evaporation of the solvent, a white solid (9.9 g) is obtained, m.p. 77° C.

EXAMPLE 433

4-(3,4-dimethoxyphenyl)-2-(4-methylphenoxy)-5-morpholinocarbonylpyrimidine (compound no. 433)

Acetonitrile (10 ml) potassium carbonate (0.5 g), paracresol (2.7 g) and the pyrimidine obtained in Example 432 (1 g) are placed in a reactor together with 3 drops of TDA—1[tris(3,6-dioxaheptyl)amine] as catalyst. The mixture in heated to 65° C. for one hour, and the solvent in evaporated. The mixture in taken up in water and extracted with ether, dried over $MgSO_4$ and evaporated. A white solid in obtained in a yield of 75%, m.p. 152° C.

Working as in Examples 423, 432 and 433 respectively, but starting from suitably substituted intermediates, the derivatives of formula (V) in which $R_{43}$ to $R_{44}$ are methoxy groups and $R_{45}$ and $R_{49}$ are hydrogen atoms, $Z_4$ and $R_{47}$ having the meanings indicated in the table below, are obtained.

| Compound no. | Process of Example no. | R47 | Z4 | m.p. | Log P |
|---|---|---|---|---|---|
| 434 | 423 | benzylthio | morpholino | 53 | 2.9 |
| 435 | 423 | 4-chlorobenzylthio | morpholino | 134 | 3.6 |
| 436 | 423 | 4-chlorophénylthio | morpholino | 147 | 3.7 |
| 437 | 422 + 432 + 433 | 4-chlorophénoxy | " | 174 | 3.7 |
| 438 | " | 4-bromophénoxy | " | 170 | 3.9 |
| 439 | " | 4-fluoro- | " | 189 | 3.1 |

-continued

| Compound no. | Process of Example no. | R47 | Z4 | m.p. | Log P |
|---|---|---|---|---|---|
| 440 | " | phénoxy 2-methyl-phénoxy | " | 136 | 3.6 |
| 441 | " | 4-Cl-3-méthyl-phénoxy | " | 176 | 4.3 |
| 433 | " | 4-CH$_3$-phénoxy | " | 152 | 3.6 |
| 442 | " | 4-CF$_3$-phénoxy | " | 54 | 3.9 |
| 444 | " | 2-chloro-phénylthio | " | 179 | 3.1 |
| 445 | " | 3-chloro-phénylthio | " | 58 | 3.6 |
| 446 | " | 2-bromo-phénylthio | " | 169 | 3.8 |
| 447 | " | 4-bromo-phénylthio | " | 158 | 3.8 |
| 448 | " | 3-fluoro-phénylthio | " | 67 | 3.1 |
| 449 | " | 4-fluoro phenylthio | " | 116 | 3.1 |
| 450 | " | 3,4-dichloro-phenylthio | " | 135 | 4.4 |
| 451 | " | 2,6-dichloro-phenylthio | " | 187 | 3.2 |
| 453 | 422 + 432 + 432 | anilino | morpholino | 210 | 3.2 |
| 454 | " | 4-chloro anilino | morpholino | 184 | 3.9 |
| 455 | " | 3,4-dichloro anilino | " | 152 | 4.6 |
| 456 | " | 2-chloro-4-bromo anilino | " | 122 | 4.8 |
| 457 | " | 3-chloro-4-fluoro anilino | " | 178 | 4.1 |
| 458 | " | piperidino | " | 150.6 | 2.6 |

EXAMPLE 501

Preparation of ethyl 2-acetyl-3-(3,4-dimethoxyphenyl)-5-phenyl-5-oxovalerate (compound no. 501)

3,4-Dimethoxychalcone (m,p,—(CH$_3$O)$_2$C$_5$H$_3$—CH=CH—CO—C$_5$H$_5$) (26.8 g; 0.1 mole) and ethyl acetoacetate (13 g; 0.1 mole) are dissolved in ethanol (300 ml). Activated baryta (1 g) is added, and the mixture stirred at 20° C. for 20 hours. The oxovalerate precipitate is filtered off, washed with ethanol and dried. Compound no. 501 (27 g; yield: 68%) is obtained, m.p. 135° C.

EXAMPLE 502

Preparation of ethyl 4-(3,4-dimethoxyphenyl)-2-methyl-6-phenylnicotinate (compound no. 502)

A mixture of compound no. 501 (20 g; 0.05 mole), ammonium acetate (7.7 g; 0.1 mole) and acetic acid (80 ml) is heated to boiling point under reflux for 5 hours. The reaction mixture is evaporated, redissolved in methylene chloride (200 ml) and washed with an aqueous sodium bicarbonate solution, then with water. The product is concentrated, dried and purified by chromatography on silica. A beige solid (8.5 g) is obtained, m.p. 82° C. (yield: 45%; compound no. 502).

EXAMPLE 503

Preparation of 4-(3,4-dimethoxyphenyl)-2-methyl-6-phenylnicotinic acid (compound no. 503)

A mixture of 10N aqueous sodium hydroxide solution (10 ml) and a solution of compound no. 502 (8.4 g; 0.022 mole) in ethanol (100 ml) is heated to boiling point under reflux for 30 hours. The reaction mixture is concentrated, dissolved in water, acidified, extracted with ethyl acetate, dried and concentrated. Compound no. 503 (4.7 g; yield: 61%) is obtained, m.p. 208° C.

EXAMPLE 504

Preparation of 4-(3,4-dimethoxyphenyl)-2-methyl-6-phenylnicotinoyl chloride (compound no. 504)

A mixture of compound no. 503 (3–5 g; 0–01 mole) and thionyl chloride (20 ml) is heated to boiling point under reflux for 1 hour. The reaction mixture is concentrated. Product no. 504, of an orangish-red colour, crystallises. Yield: 100%; m.p.=140° C.

EXAMPLE 505

Preparation of N-[4-(3,4-dimethoxyphenyl)-2-methyl-6-phenyl-nicotinoyl]morpholine (compound no. 505)

This is a product of formula (VI) with $R_{59}$=methyl, $Z_5$=morpholino, $R_{53}$=$R_{54}$=methoxy, $R_{55}$=$R_{56}$=H and $R_{57}$ C$_6$H$_5$.

Morpholine (2 ml) is added to a solution of compound no. 503 (1.2 g; 0.033 mole) in chloroform (50 ml). The mixture is left to react at 20° C. for 3 hours, then washed with water and concentrated; it is crystallised with ether, filtered and dried. Compound no. 505 (0.9 g; white powder; yield: 65%) is obtained, m.p. 176° C., log P=3.8.

EXAMPLES 506 AND 507

Compounds 506 and 507 are prepared as in Example 505, replacing the morpholine with CH$_3$—NH—C$_2$H$_5$ and with CH$_3$—NH—CH$_2$—CH$_2$—O—CH$_3$ respectively. Compound no. 506 melts at 76° C. (log P=4.2). Compound no. 507 is a syrup (log P=4.0).

EXAMPLE 601

Preparation of ethyl 2-(3,4-dimethoxyphenyl)-5-phenyl-3-furancarboxylate

A mixture of ethyl 2-(3,4-dimethoxybenzoyl-4-phenyl)-4-oxobutyrate (10 g; 0.027 mole), acetic anhydride (2.75 g; 0.027 mole), concentrated sulphuric acid (2 drops) and acetic acid (50 ml) are heated under reflux for 12 hours. The reaction medium is poured into water (500 ml). The product is extracted with ethyl acetate (300 ml) and the organic solution is washed with bicarbonate water and then pure water. The solution is dried over anhydrous magnesium sulphate and concentrated under reduced pressure; a gum is obtained which is crystallised by triturating it in heptane (50 ml). After filtration and drying, the desired product is obtained in the form of a beige powder (6.51 g; yield: 68%), m.p. 68° C. (compound no. 601.

EXAMPLE 602

2-(3,4-dimethoxyphenyl)-6-phenyl-3-furoic acid

A mixture containing the compound from Example 601 (5 g; 0.0142 mole), 10N sodium hydroxide (6 ml) and ethyl alcohol (100 ml) is heated under reflux for 1 hour. The medium is Concentrated under reduced pressure, the residue is dissolved in water (100 ml), and the aqueous solution is acidified to pH=4 by the addition of concentrated hydrochloric acid: a white solid precipitates. The precipitate is filtered off, the filter cake is washed with water and the product is dried under reduced pressure in the presence of $P_2O_5$ as dehydrating agent. The desired product (4.3 g; yield=93%) is obtained in the form of a white powder, m.p. 177° C. (compound no. 602).

EXAMPLE 603

2-(3,4-dimethoxyphenyl)-6-phenyl-3-furoyl chloride

A mixture of the product from Example 602 (2.8 g) and thionyl chloride (20 ml) is heated under reflux for 45 min. The medium is concentrated under reduced pressure: a green solid crystallises. A quantitative yield (3 g) of the product is obtained, m.p.=114° C. (compound no. 603).

EXAMPLE 604

2-(3,4-dimethoxyphenyl)-5-phenyl-N-ethyl-N-methyl-3-furancarboxamide

The chloride from Example 603 (1.51 g; 4.4 mmol) is dissolved in THF (20 ml). Methylethylamine (0.59 g; 10 mmol) is added with stirring: the amine hydrochloride precipitates immediately. Stirring is continued at normal temperature for ¼ hour, the hydrochloride is filtered off and the filtrate concentrated. The residual syrup is taken up in chloroform (100 ml). The chloroform solution is washed with water and the solution is concentrated; the product is crystallised from a mixture of diisopropyl ether and heptane. After filtration and drying, the desired compound (0.6 g; yield=37%) is obtained in the form of a beige powder, m.p.74° C. (compound no. 604).

EXAMPLE 605

N-[2-(3,4-dimethoxyphenyl)-6-(4-fluorophenyl)-3-furoyl]morpholine

A mixture containing N-[2-(3,4-dimethoxybenzoyl)-4-(4-fluorophenyl)-4-oxobutyryl]morpholine (1 g; 2.3 mmol), ethanol (20 ml) and concentrated hydrochloric acid (1 ml) is heated under reflux for 30 hours. The reaction medium is poured into water (200 ml) and the product extracted with chloroform (150 ml). The chloroform solution is washed with water, the chloroform solution is concentrated and the product is made to crystallise by triturating it in ether (20 ml). After filtration and drying, the desired product (0.08 g; yield=83%) is obtained in the form of a white powder, m.p. 168° C. (compound no. 605 ).

EXAMPLE 606

Preparation of 2-(3,4-dimethoxyphenyl)-5-(4-fluorophenyl)-3-(morpholinocarbonyl)pyrrole A mixture of:
N-[2-(3,4-dimethoxybenzoyl)-4-(4-fluorophenyl)-4-oxobutyryl]morpholine (5 g; 11.6 mmol),
ammonium acetate (1.8 g; 23.2 mmol),
acetic acid (30 ml) is heated under reflux for 12 hours.

The reaction medium is poured into water (30 ml) and the product is extracted with ethyl acetate (200 ml); the organic solution is washed with bicarbonate water, then with pure water, and the solution dried over anhydrous magnesium sulphate. The solution is concentrated, and the product recrystallised from toluene (300 ml). The desired product (1.4 g; yield=28%) is obtained in the form of a yellow powder, m.p. 190° C. (compound 606).

EXAMPLE 607

Preparation of 5-(4-fluorophenyl)-2-(3,4-dimethoxyphenyl)-1-methyl-3-(morpholinocarbonyl)pyrrole The following are dissolved in acetic acid (30 ml):
monomethylamine (0.72 g; 0.023 mole),
N-[2-(3,4-dimethoxybenzoyl)-4-(4-phenyl)-4-oxobutyryl]morpholine (0.72 g; 0.00115 mole).

The medium is taken to reflux temperature for 10 hours. The reaction medium is then poured into water (300 ml). The product is extracted with ethyl acetate (200 ml). The solution is washed with bicarbonate and then with water. It is then dried over magnesium sulphate and then concentrated. A brown solid is obtained which is recrystallised from ether.

The desired product (1.3 g; yield=26%) is recovered; m.p.=148° C. (compound 607).

EXAMPLE 608

2-(4-Chlorophenyl)-3-(3,4-dimethoxyphenyl)-4-(morpholinocarbonyl)pyrazole 1-(3,4-Dimethoxyphenyl)-3-(dimethylamino)-2-morpholinocarbonylpropenone (Example 402; 2.5 g), 4-chlorophenylhydrazine hydrochloride (2.1 g), triethylamine (1.2 g) and ethanol (100 ml) are introduced into a reactor. The mixture is heated under reflux for 8 hours 30 minutes.

The solvent is evaporated, the mixture is poured into water, extracted with ethyl acetate, dried over sodium sulphate and concentrated. After filtration on silica (eluent ethyl acetate; heptane; 90:10) a yellow solid (2.1 g) is obtained (m.p. 125° C.; yield: 60%) (compound 608).

EXAMPLE 609

4-Carbethoxy-2-(4-chlorophenyl)-3-(3,4-dimethoxyphenyl)pyrazole

Ethyl 3-(3,4-dimethoxyphenyl)-3-oxo-2-(dimethylaminoethylene)propionate (Example 401; 2.5 g) 4-chlorophenylhydrazine hydrochloride (1.49 g), triethylamine (0.82 g) and ethanol (100 ml) are introduced into a reactor. The mixture is heated under reflux for 8 hours. The solvent is evaporated, the reaction mixture is poured into water and taken up with ethyl acetate. After drying over sodium sulphate and evaporation of the solvent, a brown solid (3 g; yield: 95%) is obtained, which is used without purification (compound no. 609).

EXAMPLE 610

4-Carboxy-2-(4-chlorophenyl)-3-(3,4-dimethoxyphenyl)pyrazole

The ester obtained in Example 611 (3 g) is introduced into a reactor containing ethanol (150 ml) and treated with crushed 86% potash (1.01 g). The mixture is heated under reflux for 4 hours. The solvent is evaporated and the mixture is poured into water and acidified with a 1N hydrochloric acid solution to pH 1. The precipitate obtained is filtered off and washed with water and then with heptane; a brown powder (2.6 g; 93.5%) is obtained, which is used without purification (compound no. 610).

EXAMPLE 611

4-(N-methyl-N-ethylaminocarbonyl)-2-(4-chlorophenyl)-3-(3,4-dimethoxyphenyl)pyrazole The acid prepared in Example 610 (2.6 g) is heated with 75% strength thionyl chloride (50 ml) for 8 hours. The mixture is taken up in dichloromethane and concentrated. The oil obtained (1.4 g) is dissolved in methylene chloride (30 ml) and cooled to about 3° C. A solution of N-methyl-N-ethylamine (0.54 g) and pyridine (0.3 g) in methylene chloride (30 ml) is added, keeping the temperature lower than 5° C. The mixture is stirred for 6 hours 20 minutes at ambient temperature. It is poured into water and extracted with methylene chloride. The mixture is dried over sodium sulphate and concentrated. An orange precipitate (1.2 g; yield=82.2%) is obtained, m.p. 110° C. (compound no. 611).

EXAMPLE 612

4-(N,N-diethylaminocarbonyl)-2-(4-chlorophenyl)-3-(3,4-dimethoxyphenyl)pyrazole

The same method as in Example 611 is used, using diethylamine. Yield: 80% of an orange syrup (compound no. 612).

EXAMPLE 613

1-Benzyl-3-(3,4-dimethoxyphenyl)-4-(morpholinocarbonyl)pyrazole

The same operating method is used as in Example 608, using benzylhydrazine hydrochloride. A yellow oil (22.8%) is obtained as well as the normally expected isomer (45.7%) (compound no. 613).

EXAMPLE 614

1-(4-Bromobenzyl)-3-(3,4-dimethoxyphenyl)-4-(morpholinocarbonyl)pyrazole 3-(3,4-Dimethoxyphenyl)-4-(morpholinocarbonyl)pyrazole (0.9 g: obtained using the same operating method as in Example 608 with hydrazine hydrate), 4-bromobenzyl (0.7 g) potassium carbonate (0.4 g) and DMF (dimethylformamide; 70 ml) are introduced into a reactor. The mixture is heated to 75° C. for 5 hours 30 minutes. The mixture is poured into water, extracted with ethyl acetate, dried and concentrated. After filtration on silica, a precipitate (0.6 g; yield: 43.5%) is isolated, m.p. 122° C. (compound no. 614).

Working as in Examples 601 to 614 respectively, but starting from suitably substituted intermediates, the derivatives of formula (VII) in which $R_{610}$ is —CH=, $R_{63}$ and $R_{64}$ are methoxy groups, $R_{65}$ is a hydrogen atom and $NR_{61}R_{62}$, $K_{66}$ and $K_{67}$ have the meaning indicated below in the table, were obtained.

| Compound no. | Process described in Example | $K_{66}$ | $K_{67}$ | $NR_{61}R_{62}$ | m.p. | Log P |
|---|---|---|---|---|---|---|
| 615 | 604 | O | —C(4-chlorophenyl)= | $N(CH_3)C_2H_5$ | 102 | 4.7 |
| 616 | 605 | O | —C(4-chlorophenyl)= | morpholino | 130 | 4.3 |
| 617 | 605 | O | —C(phenyl)= | morpholino | 177 | 3.6 |
| 604 | 604 | O | —C(phenyl)= | $N(CH_3)C_2H_5$ | 74 | 4.0 |
| 605 | 605 | O | —C(4-fluorophenyl)= | morpholino | 168 | 3.7 |
| 606 | 606 | —NH— | —C(4-fluorophenyl)= | morpholino | 190 | 3.1 |
| 607 | 607 | —N(CH$_3$)— | —C(4-fluorophenyl)= | morpholino | 148 | 3.9 |
| 618 | 606 | —NH— | —C(4-chlorophenyl)= | morpholino | 225 | 3.7 |
| 619 | 607 | —N(CH$_3$)— | —C(4-chlorophenyl)= | morpholino | 155 | 4.5 |
| 620 | 606 | —N(H)— | —C(phenyl)= | morpholino | 160 | 3.0 |
| 621 | 607 | —N(CH$_3$)— | —C(phenyl)= | morpholino | 173 | 3.8 |
| 622 | 606 | —N(H)— | —C(4-butylphenyl)= | morpholino | 156 | 4.9 |
| 623 | 608 | —N(C$_6$H$_5$)— | —N= | morpholino | 110 | 2.5 |
| 624 | 611 | —N(C$_6$H$_5$)— | —N= | $N(CH_3)_2C_2H_5$ | syrup | 2.0 |
| 625 | 612 | —N(C$_6$H$_5$)— | —N= | $N(C_2H_5)_2$ | 111 | 3.4 |
| 608 | 608 | —N(4-chlorophenyl) | —N= | morpholino | 125 | 3.2 |
| 611 | 611 | —N(4-chlorophenyl) | —N= | $N(CH_3)C_2H_5$ | 110 | 3.6 |
| 612 | 612 | —N(4-chiorophenyl) | —N= | $N(C_2H_5)_2$ | syrup | 4.0 |
| 626 | 608 | —N(benzyl) | —N= | morpholino | syrup | 2.5 |
| 627 | 611 | —N(benzyl) | —N= | $N(CH_3)C_2H_3$ | 105 | 2.9 |
| 628 | 612 | —N(benzyl) | —N= | $N(C_2H_5)_2$ | syrup | 3.3 |
| 619 | 613 | —N= | —N(benzyl)— | morpholino | syrup | 2.5 |
| 614 | 614 | —N= | —N(4-bromo benzyl)— | morpholino | 122 | 3.4 |

BIOLOGICAL EXAMPLES

The following examples show the good fungicidal properties of the compounds according to the invention.

Example B1

Treatment of tomato mildew (*Phytophthora infestans*)

Tomato (*Lycopersicum esculentum*) plants, of the Marmande variety, are cultivated in pots. When these plants are a month old (5 to 6 leaf stage, height 12 to 15 cm), they are treated by spraying with a suspension or aqueous solution of the material to be tested, which is at the desired concentration and contains a surfactant which is a condensate of sorbitan monooleate with 20 molecules of ethylene oxide. This surfactant is at a concentration equal to half the concentration of the active material. Each tomato plant receives about 5 ml of the solution or dispersion. The treatment is carried out on two plants for each concentration of active material to be tested. Plants used as controls are treated with a solution which contains no active material, but contains the same surfactant at an identical concentration.

After drying for 24 hours, each plant is infected by spraying with an aqueous suspension of spores of *Phytophthora infestans*, which is responsible for tomato mildew, at a rate of about 5 ml/plant (that is about 50,000 spores per plant).

After this infection, the tomato plants are incubated for one day at about 15° C. in a saturated atmosphere, then for five days at about 17° C. and 70% to 90% relative humidity.

Seven days after infection, the results obtained in the case of plants treated with the active material to be tested are compared with those obtained in the case of plants used as controls.

In these conditions, it was observed that, at a dose of 1,000 ppm (1 g/l) compounds 104, 110, 111, 112, 113, 117, 118, 129, 133, 148, 149, 150, 164, 166, 167, 169, 201 to 203, 205, 206, 208, 209, 211, 212, 214, 222, 223, 235, 236, 237, 238, 301, 345, 347, 349, 350, 353, 356, 359, 364, 369, 370, 379, 381, 382, 384 to 386, 388, 391 and 393, 396, 3113, 3118, 3119, 407, 414 to 416, 433, 434, 435, 440, 445, 458, 505 to 507, 607, 619, 621, 608, and 6081 resulted in at least 80% inhibition of the development of the mould.

Example B2

Treatment of vine mildew (*Plasmopara viticola*)

Vine (*Vitis vinifera*) cuttings of the Chardonnay variety are cultivated in pots. When these plants are 2 months old (8 to 10 leaf stage, height 20 to 30 cm) they are treated in the same manner as in Example B1.

After drying for 24 hours, each plant is infected by spraying with an aqueous suspension of spores of *Plasmopara viticola* which is responsible for vine mildew, at the rate of about 5 ml/plant (that is about 100,000 spores per plant).

After this infection, the vine plants are incubated for two days at about 18° C. in a saturated atmosphere, then for five days at about 20°–22° C. and 90–100% relative humidity.

Eight days after infection, the results obtained in the case of the plants treated with the active material to be tested are compared with those obtained in the case of plants used as controls.

Under these conditions it was observed that at a dose of 330 ppm (0.33 g/l) compounds 101, 104, 105, 107, 110 to 118, 121 to 125, 127 to 134, 136, 137, 141, 148 to 150, 152 to 160, 162 to 164, 166 to 170, 201 to 203, 204, 205, 206, 208, 209, 210, 211, 212, 213, 214, 215, 217, 222, 223, 229, 234 to 239, 301, 345, 347, 349 to 351, 353 to 356, 358, 359, 361 to 370, 373 to 380, 382 to 391, 393 to 394, 396, 397, 399, 3100, 3112 to 3119, 407, 414 to 416, 420, 421, 433 to 442, 445, 450, 458, 505 to 507, 616, 607, 608, 612, 613, 619, 621, 623, and 626 resulted in at least 80% inhibition of the development of the mould.

Example B3

Action on phytopathogenic soil fungi

The compounds according to the invention were made to act on the following fungus:

*Phytophthora citrophthora*, a parasite of the roots of citrus fruits which is expressed by mycoses and deformations of the aerial parts.

Each experiment was carried out in the following manner: a nutrient medium based on potato extracts solidified with agar is introduced in a supercooled state into a series of Petri dishes (20 ml per dish) after sterilization in an autoclave at 120° C.

While filling the dishes, an acetone solution of the active material is injected into the supercooled medium to obtain the desired final concentration.

As control, Petri dishes analogous to those above are taken, into which are poured similar quantities of a nutrient medium which does not contain active material.

After solidification, each dish is seeded by deposition of a fragment of mycelium from a previous culture of the same fungus.

The dishes are kept at 22° C. for 5 days, and then the growth of the fungus in the dishes containing the active material to be tested is compared with that of the same fungus in the dish used as a control.

Under these conditions, at a dose of 30 ppm (parts per million) the following compounds caused at least 80% inhibition of the development of the fungus: 101, 102, 104, 105, 107, 110 to 118, 121 to 129, 131 to 137, 141, 149 to 150, 153 to 158, 162 to 164, 166, 167, 169, 201 to 203, 204, 205, 206, 208, 209, 210, 211, 212, 213, 214, 215, 216, 217, 222, 223, 224, 228, 229, 230, 231, 234 to 239, 301, 345, 347, 349, 350, 353, 354, 355, 356, 358 to 360, 363 to 370, 373, 376 to 386, 388 to 397, 3110 to 3119, 407, 414 to 416, 420, 425 to 430, 433 to 442, 445, 447, 449, 450, 458, 505 to 507, 607, 608, 619 and 621.

USE OF THE COMPOUNDS OF THE INVENTION

The compounds according to the invention can be used as active fungicidal materials, in particular for the fight against fungal diseases of plants, in particular those due to pathogenic fungi in particular those of the oomycete family of the *Phytophthora sp.* type, for example *Phytophthora infestans* (potato or tomato mildew), *Phytophthora citropthora*, *Phytophthora capsici*, *Phytophthora cactorum*, *Phytophthora palmivora*, *Phytophthora cinnamoni*, *Phytophthora megasperma*, *Phytophthora parasitica*, *Peronospora sp.* (in particular tobacco mildew), *Plasmopara sp.*, in particular *Plasmopara viticola* (vine mildew) and *Plasmopara halstedei* (sunflower mildew), *Pseudoperonospora sp.* (in particular mildew of cucurbitaceae and of hops), *Bremia lactucae* (lettuce mildew) as well as the soil fungi.

They are advantageously applied at doses from 0.01 to 5 kg/ha, and more specifically from 0.02 to about 1.5 kg/ha. For practical purposes, the compounds according to the invention are rarely used alone. Most often they are part of compositions which are usable for protection of vegetables against fungal diseases, or in plant growth-regulating compositions. The present invention accordingly provides a composition which comprises a compound of general formula (I) wherein Z is a group —NR$_1$,R$_2$ as hereinbefore defined in association with an agriculturally acceptable diluent or carrier and/or an agriculturally acceptable surfactant. In particular the usual inert supports and the usual surfactants are usable.

The term "support" designates, in the present specification, an organic or inorganic natural or synthetic material with which the active material is associated to facilitate its application to the plant, seeds or the soil. This support is therefore generally inert, and it must be acceptable in agriculture, in particular to the plant treated. The support can be solid (clays, natural or synthetic silicates, silica, resins, waxes, solid fertilizers etc.) or liquid (e.g. water, alcohols, ketones, petroleum fractions, aromatic or paraffin hydrocarbons or chlorinated hydrocarbons) or a gas.

The compositions according to the invention, (which are intended to be sold in the concentrated state or to be applied directly in the diluted state) generally contain from 0.0001 to 95% of active material, preferably from 0.0005 to 90%, as well an 0 to 20% of surfactant, preferably 0.5 to 15%. The concentrated compositions which are intended for sale generally contain 0.1 to 95% of active material, preferably 0.5 to 90%.

The surfactant can be an emulsifier, dispersing or wetting agent of the ionic or non-ionic type. For example polyacrylic acid salts, lignosulphonic acid salts, phenolsulphonic or naphthalene sulphonic acid salts, polycondensates of ethylene oxides with fatty alcohols or with fatty acids or with fatty amines, substituted phenols (in particular alkyl phenols or aryl phenols), salts of sulphosuccinic acid esters, derivatives of taurine (in particular alkyl taurates) and phosphoric esters of polyoxyethylated alcohols or phenols can be mentioned. The presence of at least one surfactant is generally indispensable when the active material and/or the inert support are not soluble in water and water is the carrying agent for application.

The compositions used in the invention can be in rather diverse forms; fluid, liquid or solid.

An forms of fluid or liquid compositions there may be mentioned in particular emulsifiable concentrates, emulsions, concentrated aqueous suspensions, pastes, solutions, in particular concentrates which are soluble in water, concentrated solutions in an organic medium (ULV=ultra low volume solutions) and aerosols.

Emulsifiable or soluble concentrates generally contain 10 to 80% of active material, emulsions or solutions ready for application themselves contain 0.001 to 20% of active material. In addition to the active material and the solvent, emulsifiable concentrates can contain, when necessary, an appropriate co-solvent and from 2 to 20% of appropriate additives, such as stabilizers, penetrating agents, corrosion inhibitors, colourings and adhesives.

From these concentrates, emulsions of any desired concentration can be obtained by dilution with water, which is particularly suitable for application to arable land. For example, here is the composition of some emulsifiable concentrates:

Examples CE 1

| | |
|---|---|
| active material | 250 g/l |
| (compound no. 101 or 202 or 301 | |
| epoxidised vegetable oil | 25 g/l |
| mixture of alkylarylsulphonate and | 100 g/l |
| polyglycol ether and fatty alcohols | |
| dimethylformamide | 50 g/l |
| xylene | 575 g/l |

| | |
|---|---|
| active material | 400 g/l |
| (compound no. 105 or 206 or 345) | |
| alkaline dodecylbenzenesulphonate | 24 g/l |
| nonlylphenol polycondensed with 10 molecules | 16 g/l |
| of ethylene oxide | |
| cyclohexanone | 200 g/l |
| aromatic solvent | 1 l |

Emulsions of any desired concentration can be obtained from these concentrates by dilution with water, which is particularly suitable for application to leaves.

Concentrated suspensions, which can also be applied by spraying, are prepared so as to obtain a stable fluid product which does not sediment out, and they normally contain from 10 to 75% of active material, from 0.5 to 145% of surfactant agents, from 0.1 to 10% of thixotropic agents and from 0 to 10% of appropriate additives, such an antifoams, corrosion inhibitors, stabilizers, penetrating agents and adhesives, and, as support, water or an organic liquid in which the active material is only slightly soluble or insoluble: certain solid organic materials or inorganic salts can be dissolved in the support to help to hinder sedimentation, or as antifreezes for the water.

For example, here is the composition of several concentrated aqueous suspensions according to the invention:

Example SAC 1

| | |
|---|---|
| active material | 100 g/l |
| (compound no. 106 or 206 or 350) | |
| wetting agent (polycondensate of | 5 g/l |
| ethylene oxide with alkyl phenol) | |
| dispersing agent | 10 g/l |
| (Na naphthalenesulphonate) | |
| antifreeze (propylene glycol) | 100 g/l |
| thickener (polysaccharide) | 3 g/l |
| biocide (formaldehyde) | 1 g/l |
| water | qs 1 liter |

Example SAC 2

An aqueous suspension is prepared containing:

| | |
|---|---|
| active material | 250 g/l |
| (compound no. 108 or 208 or 301) | |
| wetting agent (polycondensate of ethylene | 10 g/l |
| oxide with a C$_{13}$ synthetic alcohol) | |
| dispersing agent (sodium lignosulphonate) | 15 g/l |
| antifreeze (urea) | 50 g/l |
| thickener (polysaccharide) | 2.5 g/l |
| biocide (formaldehyde) | 1 g/l |
| water | qs 1 liter |

Example SAC 3

An aqueous suspension is prepared containing:

| | |
|---|---|
| active material (compound no. 109 or 209 or 345) | 500 g/l |
| wetting agent (polycondensate of ethylene oxide with a $C_{13}$ synthetic alcohol) | 10 g/l |
| dispersing agent (salified condensate of ethylene oxide with polyarylphenolphosphate | 50 g/l |
| antifreeze (propylene glycol) | 100 g/l |
| thickener (polysaccharide) | 1.6 g/l |
| biocide (sodium 4-methylhydroxybenzoate) | 3.3 g/l |
| water | qs 1 liter |

As forms of solid compositions, there may be mentioned powders for powdering (with an active material content which can go up to 100%) and granules, in particular those obtained by extrusion, by compaction, by impregnation of a granulated support or by granulation from a powder (the content of compound of formula (I) in these granules being between 0.5 and 80% for the latter cases).

Wettable powders, (or powders for spraying) are normally prepared such that they contain 10 to 95% of active material, and they normally contain, in addition to a solid support, from 0 to 5% of a wetting agent, from 3 to 10% of a dispersing agent, and, when necessary, from 0 to 10% of one or more stabilizers and/or other additives, such as penetration agents, adhesives, or anti-caking agents, colourings and the like.

For example, here is the composition of some wettable powders.

Example PM1

| | |
|---|---|
| active material (compound no. 111 or 211 or 350) | 10% |
| synthetic $C_{13}$ oxo-alcohol of the branched type, condensed with 8 to 10 mols ethylene oxide (wetting agent) | 0.75% |
| neutral calcium lignosulphonate (dispersing agent) | 12% |
| calcium carbonate (inert filler) | qs 100% |

Example PM 2

| | |
|---|---|
| active material (compound no. 102 or 202 or 301 according to the invention) | 50% |
| condensate of ethylene oxide with a fatty alcohol (wetting agent) | 2.5% |
| condensate of ethylene oxide with styrylphonol (dispersing agent) | 5% |
| chalk (inert support) | 42.5% |

Example PM 3 containing the same ingredients as in the preceding example, in the following proportions:

| | |
|---|---|
| active material (compound no. 105 or 206 or 345) | 75% |
| wetting agent | 1.5% |
| dispersing agent | 8% |
| calcium carbonate (inert filler) | qs 100% |

Example PM4

| | |
|---|---|
| active material (compound no. 106 or 206 or 350) | 90% |
| condensate of ethylene oxide with a fatty alcohol (wetting agent) | 4% |
| condensate of ethylene oxide with styrylphenol (dispersing agent) | 6% |

To obtain these spraying powders or wettable powders, the active material is mixed intimately in appropriate mixers with the additional substances, and the mixture is ground with mills or other appropriate grinders. In this way sprayable powders are obtained, the wettability and suspendability of which are advantageous; they can be suspended in water at any desired concentration, and this suspension is very advantageously usable, in particular, for application to the leaves of plants.

The compounds of formula (I) can in addition be used in the form of powders for dusting; a composition containing active material (50 g) and talc (950 g) can also be used; a composition containing active material (20 g), finely divided silica (10 g) and talc (970 g) can also be used; these constituents are mixed and ground, and the mixture is applied by dusting.

Granules for dusting have sizes of between 0.1 and 2 mm, and can be manufactured by agglomeration or impregnation. Generally, granules contain 0.5 to 25% of active material, and 0 to 10% additives such as stabilizers, modification agents for slow liberation, binders and solvents.

Here are two examples of granule compositions:

Examples G 1 and G 2

| | | |
|---|---|---|
| active material (compound no. 108 or 208 or 301) | 50 g | 200 g |
| propylene glycol | 50 g | 50 g |
| cetyl and polyglycol ether | 2.5 g | 2.5 g |
| polyethylene glycol | 35 g | 35 g |
| kaolin (particle size: 0.3 to 0.8 mm) | 910 g | 760 g |

The compounds according to the invention can advantageously be formulated in the form of granules which are dispersible in water, which are also included within the scope of the invention.

These dispersible granules, of apparent density generally about 0.3 and 0.6, have a particle size generally between about 150 and 2,000 microns, and preferably between 300 and 1500 microns.

The active material content of these granules is generally between about 1% and 90%, and preferably between 25% and 90%.

The remainder of the granule is essentially composed of a solid filler, and optionally of surfactant additives conferring properties of dispersibility in water on the granules. These granules can essentially be of two distinct types according to whether the filler is soluble or insoluble in water. In the case of a water-soluble filler, it can be inorganic and preferably organic. Excellent results have been obtained with urea. In the case of an insoluble filler, this is preferably inorganic, such as, for example, kaolin or bentonite. It is then accompanied by surfactant agents (at a rate of 2 to 20% by weight of the granule) surfactant additives more than half of which is constituted by at least one dispersing agent which is essentially anionic, such as an alkali or alkaline-earth poly(naphthalenesulfonate) or an alkali or alkaline-earth lignosulfonate. The remainder being constituted by non-ionic or anionic wetting agents such as an alkali or alkaline-earth alkylnaphthalenesulfonate.

In addition, although it is not indispensable, other adjuvants such as anti-foam agents can be added.

The granules according to the invention can be prepared by mixing the necessary ingredients and then granulation by several techniques which are known per se (ball granulator, fluidized bed, atomizer, extrusion, and the like). The process is generally ended by crushing followed by sieving to the chosen particle size within the limits mentioned above.

Preferably, the granules according to the invention are obtained by extrusion. Working as indicated in the following examples, the following compositions of dispersible granules were prepared.

Example GD1

Active material (compound no. 111 or 211; 90% by weight) and urea beads (10%) are mixed in a mixer. The mixture is then ground in a toothed roll crusher. A wet powder is obtained which is extruded in a perforated roll extruder. Granules are obtained which are dried, then crushed and sieved, so that only the granules of a size between 150 and 2000 microns respectively are kept.

Example GD2

The following constituents are mixed in a mixer:

| | |
|---|---|
| active material (compound no. 105 or 202 or 345) | 75% |
| wetting agent (sodium alkylnaphthalenesulfonate) | 2% |
| dispersing agent (sodium polynaphthalenesulfonate) | 8% |
| inert filler which is insoluble in water (kaolin) | 15% |

Example GD3

| | |
|---|---|
| active material (compound no. 105 or 206 or 350) | 20% |
| sodium alkylnaphthalenesulfonate | 2% |
| sodium methylene-bis-naphthalenesulfonate | 8% |
| kaolin | 70% |

This mixture is granulated in a fluidized bed in the presence of water, then dried, crushed and sieved so as to obtain granules of a size between 0.16 and 0.40 mm.

These granules can be used alone, in solution or dispersion in water in such a manner as to obtain the required dose. They can also be used to prepare associations with other active materials, in particular fungicides, these latter being in the form of wettable powders or of granules or aqueous suspensions.

The compounds according to the invention can also be formulated in the form of organic solutions which are capable of being encapsulated, in particular by interfacial polymerization, in capsules with polymeric walls, for example based on polyamides, polyureas or polyamideureas. These capsules are found in the state of a concentrated aqueous dispersion which can be diluted at the time of use to obtain a slurry for spraying.

As has already been said, aqueous dispersions and emulsions, for example the compositions obtained by diluting a wettable powder or an emulsifiable concentrate according to the invention with water, are within the general scope of the compositions which are usable in the present invention. The emulsions can be of the water-in-oil or oil-in-water type, and they have a thick consistency like that of a "mayonnaise".

In addition the invention relates to the treatment of plants against diseases caused by phytopathogenic fungi, in particular those of the oomycete family of the *Phytophthora sp.* type, for example *Phytophthora infestans* (potato or tomato mildew), *Phytophthora citrophthora*, *Phytophthora capsici*, *Phytophthora cactorum*, *Phytophthora palmivora*, *Phytophthora cinnamoni*, *Phytophthora megasperma*, *Phytophthora parasitica*, *Peronospora sp.* (in particular tobacco mildew), *Plasmopara sp.*, in particular *Plasmopara viticola* (vine mildew) and *Plasmopara halstedei* (sunflower mildew), *Pseudoperonospora sp.* (in particular mildew of cucurbitaceae and hops), *Bremia lactucae* (lettuce mildew) as well as soil fungi.

This invention provides a method of combatting fungal attack of plants at a locus which comprises applying thereto a compound of general formula (I) wherein Z represents a group —$NR_1R_2$ as hereinbefore defined. It will be understood that an effective quantity of the compound of formula (I) will be used: by "effective quantity" is understood a quantity which is sufficient to allow control and destruction of the fungi present on the plants. The doses to be used can, however, vary within wide limits according to the fungus to be combatted, the type of crop, the climatic conditions and according to the compound used.

In practice doses varying from 1 g/hl to 500 g/hl, corresponding approximately to doses of active material per hectare of 10 g/ha to about 5000 g/ha generally give good results.

As examples of methods treatment which can be used, there may be mentioned spraying of leaves or soil, dusting, soaking, the incorporation of granules, powders or slurries in the soil, watering, injection into trees, painting and the treatment of seeds.

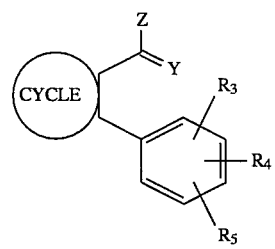

FORMULA I

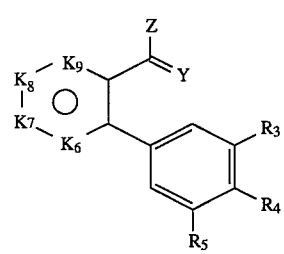

FORMULA Ia

-continued
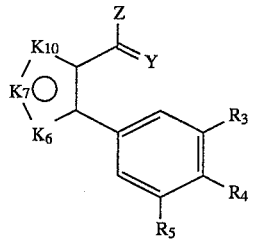
FORMULA Ib
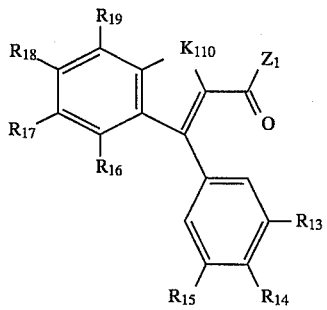
FORMULA II
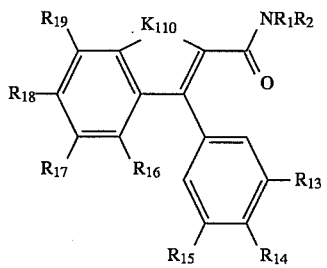
FORMULA II'
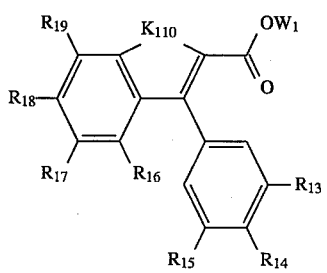
FORMULA II''
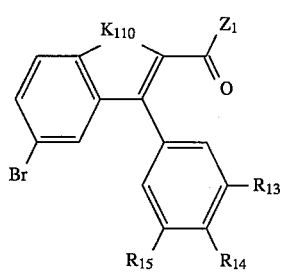
FORMULA II'''
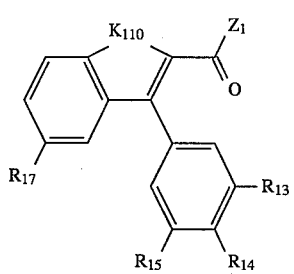
FORMULA II''''
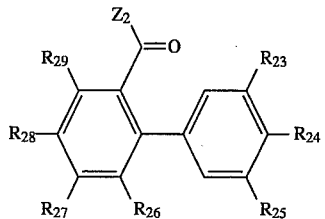
FORMULA III
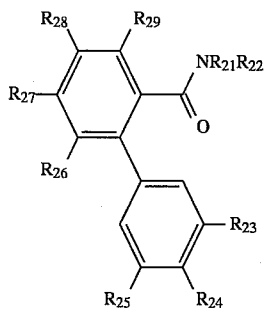
FORMULA III'
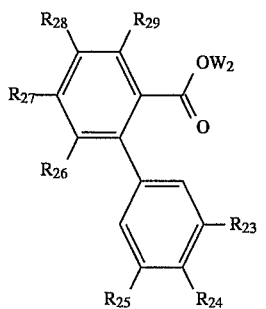
FORMULA III''
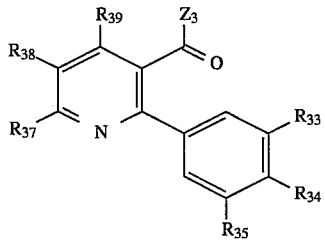
FORMULA IV
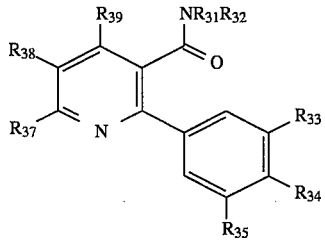
FORMULA IV'
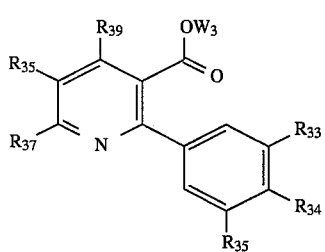
FORMULA IV''

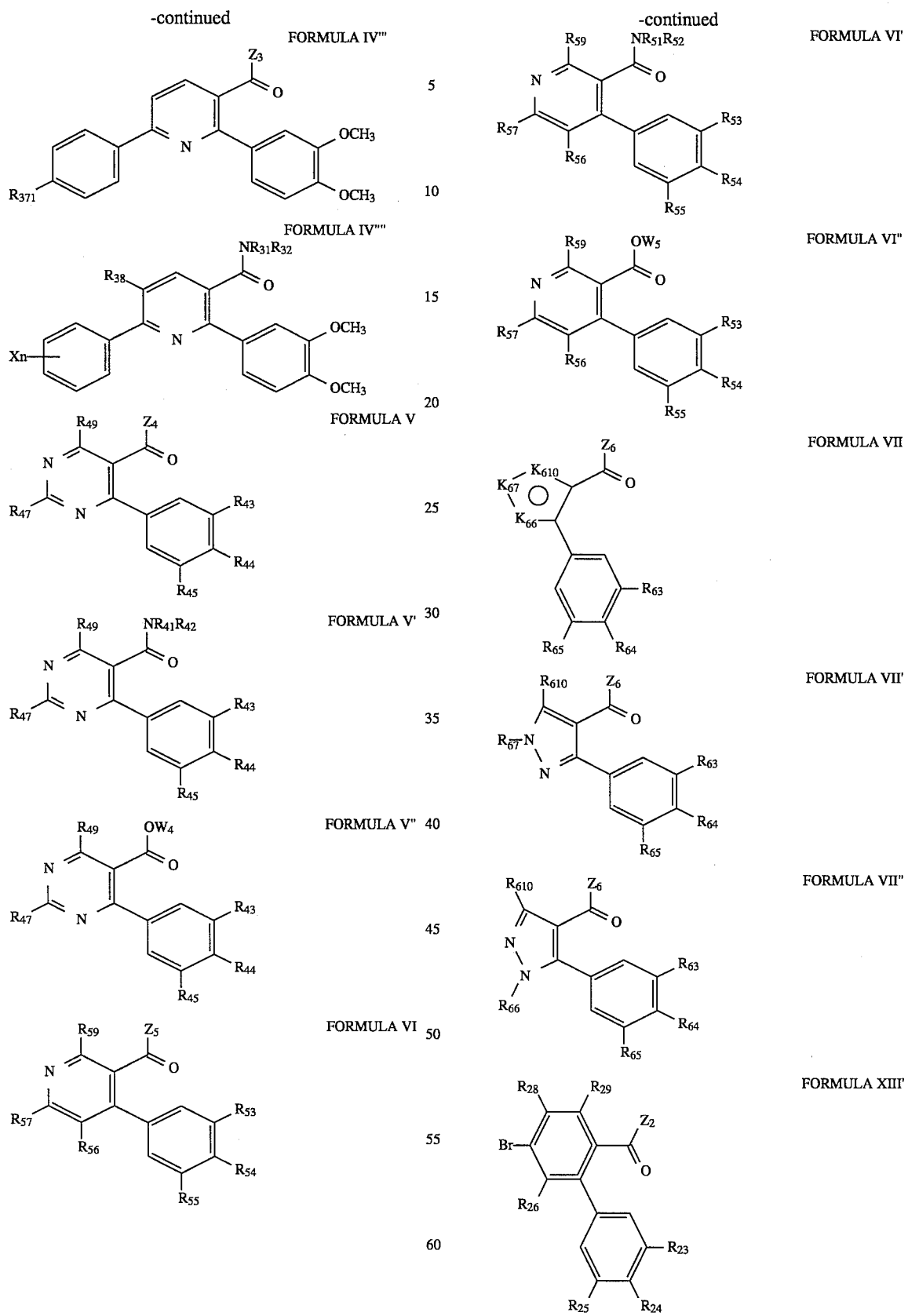

-continued
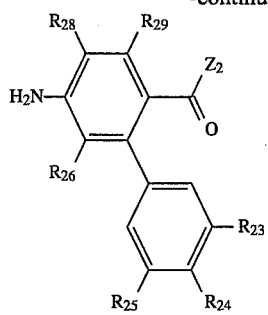
FORMULA XIII"
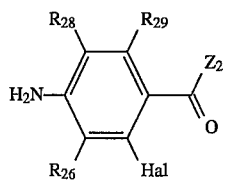
FORMULA XIII'"
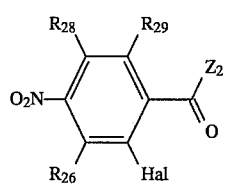
FORMULA XIII""
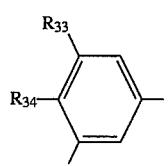
FORMULA XIV"
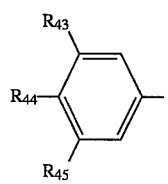
FORMULA XV"
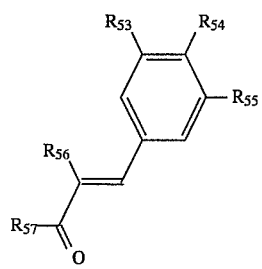
FORMULA XVI'
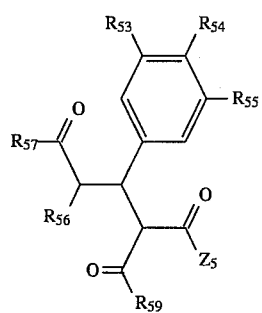
FORMULA XVI"
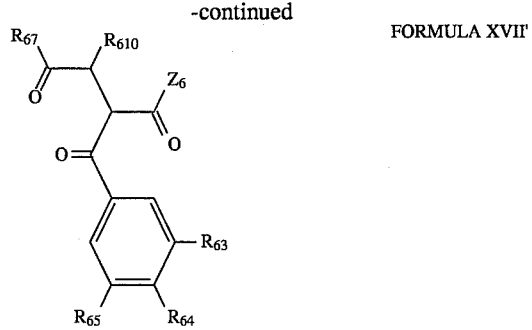
FORMULA XVII'
FORMULA XVII'"
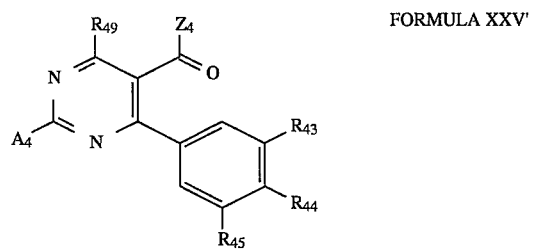
FORMULA XXV'
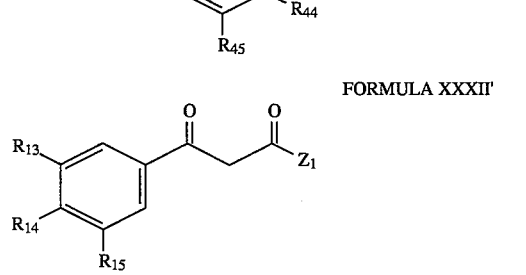
FORMULA XXXII'
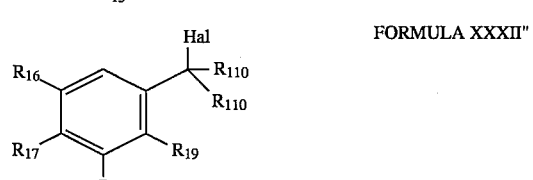
FORMULA XXXII"
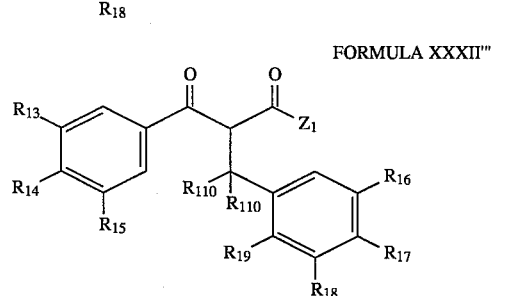
FORMULA XXXII'"
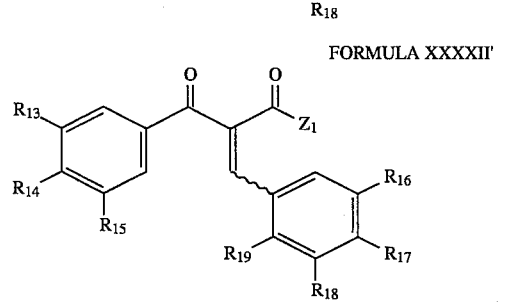
FORMULA XXXXII'

-continued

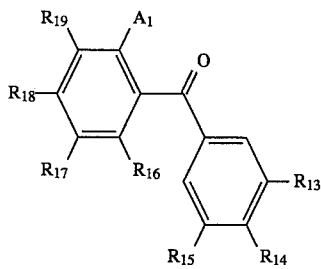

FORMULA XII'

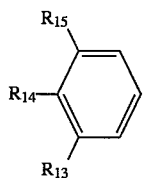

FORMULA XII"

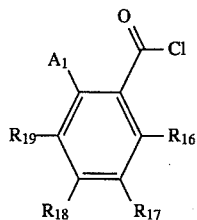

FORMULA XII'''

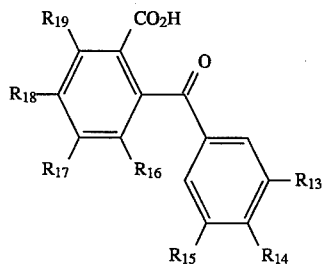

FORMULA XXII'

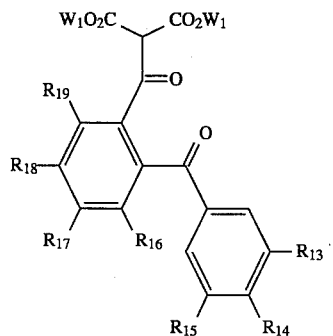

FORMULA XXII"

We claim:

1. A compound having the formula

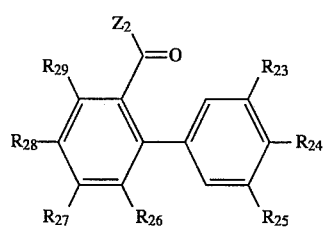

(III)

wherein:

$Z_2$ is $OW_2$ wherein $W_2$ is a hydrogen atom, a lower alkyl radical or an alkali metal or alkaline earth metal atom;

$R_{23}$ is methoxy and $R_{24}$ is methoxy, or $R_{23}$ and $R_{24}$ together form a methylenedioxy or ethylenedioxy group, the carbon atoms of which are optionally substituted by lower alkyl or halogen:

$R_{25}$ represents:

a hydrogen or halogen atom;

an amino group which is optionally substituted by one or two lower alkyl groups;

a lower alkyl, lower alkoxy, (lower)alkoxy-(lower)alkyl or lower alkylthio group, each of which is optionally halogenated or hydroxylated;

$R_{26}$ and $R_{27}$, which are identical or different, each represent:

hydrogen or halogen, at least one of $R_{26}$ and $R_{27}$ being other than hydrogen;

cyano, nitro, thiocyanato, hydroxyl or carboxyl;

alkyl, cycloalkyl, alkenyl, alkynyl, alkyl-$S(O)_n$ (wherein n is 0, 1 or 2), alkoxy, cycloalkoxy, alkenyloxy or alkynyloxy, each of which has up to 8 carbon atoms and is optionally substituted by one or more halogen atoms;

(lower)alkoxy-carbonyl, CO—NR'R", NR'R", N(R')—OC—R", O—CO—R' or O—CO—NR'R"; or phenyl, naphthyl, phenyl-$S(O)_n$ (wherein n is 0, 1 or 2), phenoxy, phenyl-(lower)alkyl, phenyl-(lower)alkyl-$S(O)_n$ (wherein n is 0, 1 or 2), phenyl-(lower)alkoxy or thienyl, the phenyl or thienyl rings being unsubstituted or substituted by:

halogen;

nitro, cyano, carboxyl, hydroxyl, mercapto, thiocyanato, (lower)alkoxy-carbonyl, —CO—NR'R", —NR'R", —N(R')—CO—R", —O—CO—R' or —O—CO—NR'R"; or lower alkyl, lower alkoxy, (lower)alkyl-$S(O)_n$ (wherein n is 0, 1 or 2), cycloalkyl having 3 to 7 carbon atoms, phenyl, phenoxy, phenyl-$S(O)_n$ (wherein n is 0, 1 or 2), phenylalkyl, phenylalkoxy or phenylalkyl-$S(O)_n$ (wherein n is 0, 1 or 2), which is optionally halogenated and has 1 to 4 carbon atoms in the alkyl portion;

R' and R", which are identical or different, each represent hydrogen; lower alkyl; cycloalkyl having 3 to 7 carbon atoms; optionally halogenated phenyl; optionally halogenated phenyl-(lower)alkyl; alkenyl or alkynyl having 3 to 7 carbon atoms; or alkoxyalkyl having 3 to 8 carbon atoms; and $R_{28}$ and $R_{29}$, which are identical or different, each represent hydrogen or halogen; hydroxyl; lower alkyl; lower alkoxy; (lower)alkoxy-(lower)alkyl; or (lower)alkoxycarbonyl;

with the proviso that when $R_{28}$ represents hydroxyl and $R_{26}$ represents methyl, then $W_2$ is other than hydrogen.

2. A compound according to claim 1, having the formula

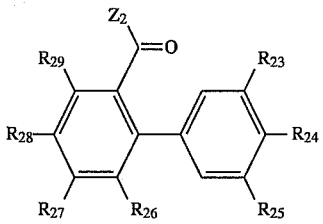
(III)

wherein:

$Z_2$ is $OW_2$ wherein $W_2$ is a hydrogen atom, a lower alkyl radical or an alkali metal or alkaline earth metal atom;

$R_{23}$ is methoxy and $R_{24}$ is methoxy;

$R_{25}$ represents hydrogen or halogen, lower alkyl, lower alkoxy or lower alkylthio;

$R_{26}$ and $R_{27}$, which are identical or different, each represent hydrogen or halogen, lower alkyl, lower alkenyl, lower alkoxy, lower alkylthio, lower halogenoalkyl, lower halogenoalkoxy or lower halogenoalkylthio, at least one of $R_{26}$ and $R_{27}$ being other than hydrogen; and $R_{28}$ and $R_{29}$, which are identical or different, each represent hydrogen or fluorine.

3. A compound according to claim 1, wherein $R_{23}$ is methoxy and $R_{24}$ is methoxy.

4. The compound according to claim 3, wherein $R_{25}$ is hydrogen, $R_{26}$ is hydrogen, $R_{27}$ is bromo, $R_{28}$ is hydrogen, $R_{29}$ is hydrogen and $Z_2$ is ethoxy.

5. The compound according to claim 3, wherein $R_{25}$ is hydrogen, $R_{26}$ is hydrogen, $R_{27}$ is bromo, $R_{28}$ is hydrogen, $R_{29}$ is hydrogen and $Z_2$ is hydroxy.

6. The compound according to claim 3, wherein $R_{25}$ is hydrogen, $R_{26}$ is nitro, $R_{27}$ is hydrogen, $R_{28}$ is hydrogen, $R_{29}$ is hydrogen and $Z_2$ is hydroxy.

* * * * *